(12) United States Patent
Yoshida et al.

(10) Patent No.: US 6,319,879 B1
(45) Date of Patent: Nov. 20, 2001

(54) DERIVATIVE OF BICYCLO [2.2.1] HEPTANE, METHOD FOR ITS PRODUCTION, AND FLUID FOR TRACTION DRIVE

(75) Inventors: Yukio Yoshida; Toshiyuki Tsubouchi; Motohisa Ido, all of Sodegaura; Hitoshi Hata, Ichihara, all of (JP)

(73) Assignee: Idemitsu Kosan Co., Ltd. (JP)

( * ) Notice: Subject to any disclaimer, the term of this patent is extended or adjusted under 35 U.S.C. 154(b) by 0 days.

(21) Appl. No.: 09/340,034

(22) Filed: Jun. 28, 1999

Related U.S. Application Data
(60) Provisional application No. 60/103,155, filed on Oct. 2, 1998.

(30) Foreign Application Priority Data
Jul. 1, 1998 (JP) .................................................. 10-186399

(51) Int. Cl.[7] .............................................. C10M 105/04
(52) U.S. Cl. .............................. 508/110; 252/73; 585/10; 585/20
(58) Field of Search ................................ 508/110; 252/73; 585/10, 20

(56) References Cited
U.S. PATENT DOCUMENTS

| | | | |
|---|---|---|---|
| 4,975,215 | * 12/1990 | Abe | 252/73 |
| 5,107,041 | * 4/1992 | Abe et al. | 582/20 |
| 5,126,065 | * 6/1992 | Tsubouchi et al. | 585/10 |
| 5,283,384 | * 2/1994 | Abe et al. | 585/22 |

* cited by examiner

*Primary Examiner*—Margaret Medley
(74) *Attorney, Agent, or Firm*—Parkhurst & Wendel, LLP

(57) ABSTRACT

Derivatives of bicyclo[2.2.1]heptane in the invention have a high traction coefficient under high temperature and an excellent viscosity characteristic under low temperature and are useful for the fluid for a traction drive, and a method in the invention produces such derivatives economically and efficiently.

19 Claims, 15 Drawing Sheets

DERIVATIVE OF BICYCLO [2.2.1] HEPTANE, METHOD FOR ITS PRODUCTION, AND FLUID FOR TRACTION DRIVE

This application claims benefit of Provisional Application No. 60/103,155 filed Oct. 2, 1998.

TECHNICAL FIELD OF THE INVENTION

The present invention relates to a derivative of bicyclo [2.2.1]heptane with a special structure, and particularly to a derivative of bicyclo[2.2.1]heptane with a special structure having a high traction coefficient under high temperature and an excellent viscosity characteristic under low temperature and therefore useful for fluid for a traction drive, and a method for production of such the useful derivative of bicyclo[2.2.1]heptane with a special structure economically and efficiently.

In addition, the invention relates to fluid for a traction drive, and particularly fluid for a traction drive having a high traction coefficient under high temperature and an excellent viscosity characteristic under low temperature.

RELATED ART

Fluid for a traction drive is used in such machine for traction drive as a continuously variable transmission for automobiles and a continuously variable transmission for industry as a lubricating oil to drive them.

A traction coefficient required for the fluid for traction drive is generally known as depending on the size of the traction drive. The fluid for traction drive with a higher traction coefficient is required for developing a small and light traction drive machine.

For example, in CVT (continuously variable transmission) of traction type that is developed as a continuously variable transmission for automobiles, the fluid for traction drive used for CVT requires to have enough high traction coefficient under high temperature to reach, for example, the lowest within a range of applied temperature than a designed temperature for CVT in order to make size of the CVT small and increase the capacity of its torque transmission.

Besides, the fluid for traction drive requires various performances other than the higher traction coefficient.

A low viscosity, for example, 150 MPa·s or lower is required, for example, in −40° C. to keep excellent starting performance in a cold region.

On the other hand, it is required to suppress volatilization of base oil and keep enough thickness of an oil layer for use under high temperature.

Among them, increasing the traction coefficient under the high temperature does not support decreasing the viscosity under the low temperature. Developing traction oil to realize both these performances was very difficult. Against such background, the inventors of the invention enthusiastically studied and discovered a group of compounds excellent in the traction coefficient under the high temperature (the publication of unexamined applications, Koukai Publication 1995-103387). However, those compounds showed insufficient characteristics of viscosity under the low temperature.

SUMMARY OF THE INVENTION

The invention was achieved in the view aforementioned and for the purpose of providing a derivative of bicyclo [2.2.1]heptane with a high traction coefficient under high temperature and an excellent viscosity characteristic under low temperature and useful for the fluid for a traction drive and also providing a method for producing such derivative economically and efficiently.

Besides, the invention was achieved for the purpose of providing the fluid for traction drive, having a high traction coefficient under high temperature and an excellent viscosity characteristic under low temperature.

As a result of a research series of the inventors, who discovered that derivative of bicyclo[2.2.1]heptane with a special structure having a special structure shows particularly excellent performances as the fluid for traction drive and that the derivative of bicyclo[2.2.1]heptane can be economically and efficiently prepared by dimerization of a special olefinic alicyclic ring compound as a material under a special reaction condition and then by hydrogenation.

In addition, the inventors found as a result of a series of research that a synthetic oil with a special property shows excellent performances as the fluid for traction drive.

The invention has been completed based on these findings.

The followings are the abstract of the invention.

(1) At least one of any compounds of cyclo[2.2.1]heptane, exo-2-methyl-exo-3-methyl-endo-2-[(endo-2-methylbicyclo[2.2.1]hept-exo-3-yl)methyl]bicyclo[2.2.1] heptane, endo-2-methyl-exo-3-methyl-exo-2-[(exo-3-methylbicyclo-[2.2.1]hept-exo-2-yl)methyl]bicyclo[2.2.1] heptane, endo-2-methyl-exo-3-methyl-exo-2-[(exo-2-methylbicyclo[2.2.1]hept-exo-3-yl)methyl]bicyclo[2.2.1] heptane, endo-2-methyl-exo-3-methyl-exo-2-[(exo-3-methylbicyclo[2.2.1]hept-exo-2-yl)methyl]bicyclo[2.2.1] heptane, endo-2-methyl-exo-3-methyl-exo-2-[(endo-3-methylbicyclo[2.2.1]hept-endo-2-yl)methyl]bicyclo[2.2.1] heptane, or endo-2-methyl-exo-3-methyl-exo-2-[(endo-2-methylbicyclo[2.2.1]hept-endo-3-yl)methyl]bicyclo[2.2.1] heptane, particularly the mixture of exo-2-methyl-exo-3-methyl-endo-2-[(endo-3-methylbicyclo[2.2.1]hept-exo-2-yl)methyl]bicyclo[2.2.1]heptane and exo-2-methyl-exo-3-methyl-endo-2-[(endo-2-methylbicyclo[2.2.1]hept-exo-3-yl)methyl]bicyclo[2.2.1]heptane, the mixture of endo-2-methyl-exo-3-methyl-exo-2-[(exo-3-methylbicyclo[2.2.1] hept-exo-2-yl)methyl]bicyclo[2.2.1]heptane and endo-2-methyl-exo-3-methyl-exo-2-[(exo-2-methylbicyclo[2.2.1] hept-exo-3-yl)methyl]bicyclo[2.2.1]heptane, or the mixture of endo-2-methyl-exo-3-methyl-exo-2-[(endo-3-methylbicyclo[2.2.1]hept-endo-2-yl)methyl]bicyclo[2.2.1] heptane and endo-2-methyl-exo-3-methyl-exo-2-[(endo-2-methylbicyclo[2.2.1]hept-endo-3-yl)methyl]bicyclo[2.2.1] heptane.

(2) A method for producing derivative of bicyclo[2.2.1] heptane represented by the following formula (VII)

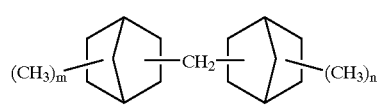

(VII)

(In the formula, m represents 2 or 3 and n represents 1 or 2). and characterized by dimerizing a bicyclo[2.2.1]heptane ring compound such as 2-methylene-3-methylbicyclo[2.2.1] heptane, 3-methylene-2-methylbicyclo[2.2.1]heptane, etc., of which methylene group and methyl group were substituted and/or a bicyclo[2.2.1]heptene ring compound such as 2,3-dimethylbicyclo[2.2.1]hept-2-ene, etc., of which methyl group was substituted, under the presence of an acid catalyst, preferably a Lewis acid, at 60° C. or lower temperature and hydrogenating the produced dimer under the presence of a catalyst for hydrogenation preferably a nickel catalyst at 200–300° C.

(3) Fluid for a traction drive, characterized by consisting of a synthetic oil having physical properties described the following (a) to (f).
  (a) molecular weight: 210 or larger.
  (b) kinematic viscosity at 40° C.: 10–25 mm$^2$/s
  (c) viscosity index: 60 or higher
  (d) pour point: −40° C. or lower
  (e) density at 20° C.: 0.93 g/cm$^3$ or higher
  (f) traction coefficient at 140° C.: 90% or higher of the coefficient of 2,4-dicyclohexyl-2-methylpentane (4) Fluid for a traction drive according to (3), wherein a synthetic oil is hydrogenated dimer of at least one alicyclic compound selected from bicyclo[2.2.1]heptane ring compounds, bicyclo[3.2.1]octane ring compounds, bicyclo[3.3.0]octane ring compounds, and bicyclo[2.2.2]octane ring compounds.

(5) Fluid for a traction drive according to (3), wherein a synthetic oil is a compound represented by the following general formula (VIII).

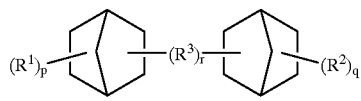

(VIII)

(In the formula, both R$^1$ and R$^2$ represent hydrogen atoms or alkyl groups with carbon numbers of 1–3, R$^3$ represents a methylene group, an ethylene group, or a trimethylene group that may be substituted by a methyl group or an ethyl group in a side chain, r represents 0 or 1, and both p and q represent integral numbers of 1–3).

(6) Fluid for a traction drive consisted of a derivative of bicyclo[2.2.1]heptane represented by the following formula (VII).

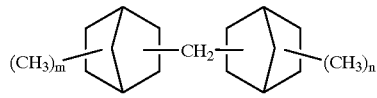

(VII)

(In the formula, m represents 2 or 3 and n represents 1 or 2).

(7) Fluid for a traction drive consisted of at least one compound selected from the group of compounds according to (1).

DETAILED DESCRIPTION OF THE PREFERRED EMBODIMENTS

Figure 1:
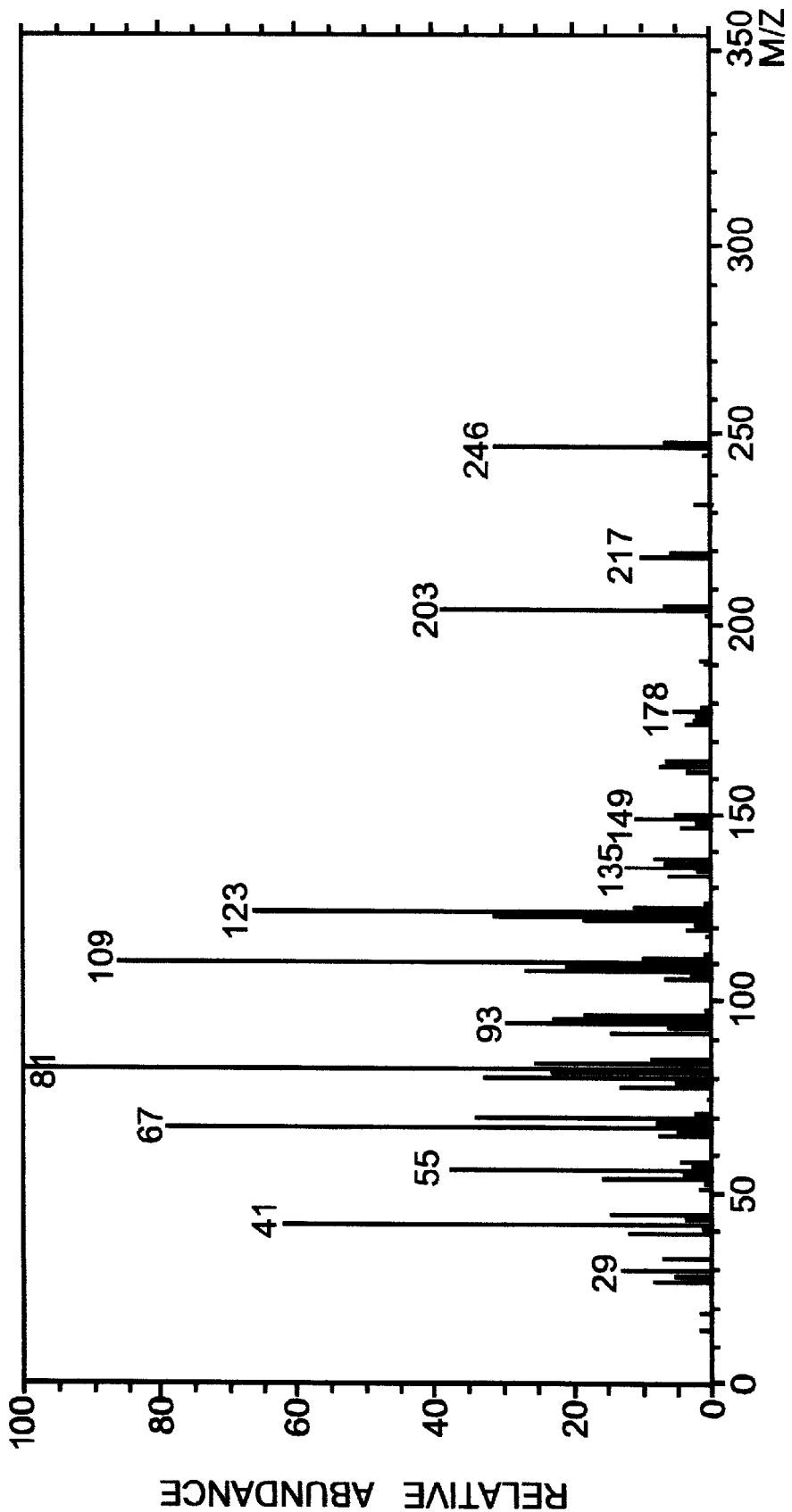
FIG. 1. A mass chromatogram of component A.

Below will be fully described the invention.

1. A Derivative of Bicyclo[2.2.1]heptane

The present invention is a derivative of bicyclo[2.2.1]heptane with a special structure, exemplified by bicyclo[2.2.1]heptane, exo-2-methyl-exo-3-methyl-endo-2-[(endo-2-methylbicyclo[2.2.1]hept-exo-3-yl)methyl]bicyclo[2.2.1]heptane, exo-2-methyl-exo-3-methyl-endo-2-[(endo-3-methylbicyclo[2.2.1]hept-exo-2-yl)methyl]bicyclo[2.2.1]heptane, endo-2-methyl-exo-3-methyl-exo-2-[(exo-3-methylbicyclo-[2.2.1]hept-exo-2-yl)methyl]bicyclo[2.2.1]heptane, endo-2-methyl-exo-3-methyl-exo-2-[(exo-2-methylbicyclo[2.2.1]hept-exo-3-yl)methyl]bicyclo[2.2.1]heptane, endo-2-methyl-exo-3-methyl-exo-2-[(endo-3-methylbicyclo[2.2-l]hepto-endo-2-yl)methyl]bicyclo[2.2.1]heptane, or endo-2-methyl-exo-3-methyl-exo-2-[(endo-2-methylbicyclo[2.2.1]hept-endo-3-yl)methyl]bicyclo[2.2.1]heptane.

These compounds are separately represented by one of the following chemical structural formula (I) to the formula (VI).

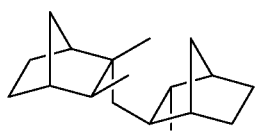

(I)

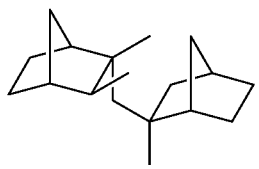

(II)

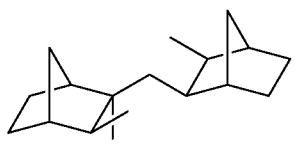

(III)

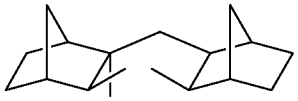

(IV)

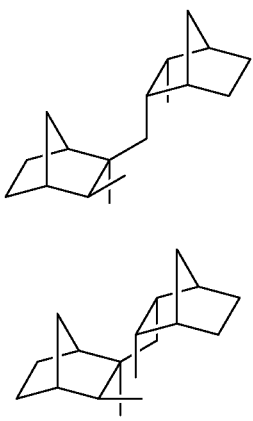

(V)

(VI)

These bicyclo[2.2.1]heptane derivatives have particularly high traction coefficient under high temperature and an excellent characteristic of viscosity under low temperature to allow preferably to use as a CVT oil for a traction drive in the world from cold and tropical regions and in addition, is a compound having very high value for use for the purpose of decreasing the CVT for the traction drive.

These compounds are included in bicyclo[2.2.1]heptane derivatives represented by the formula (VII) and prepared by the same method as production method of bicyclo[2.2.1] heptane derivatives represented by the following described formula (VII)

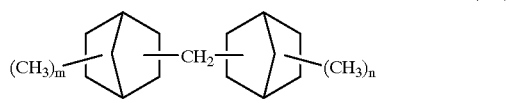

(VII)

using a material compound suitably selected. The chemical structure of these compounds is determined by analysis of each spectrogram of mass chromatogram, $^1$H-NMR, $^{13}$C-NMR, C—$^{13}$C-NMR, and $^1$H—$^{13}$C-NMR.

2. A Method for Producing Bicyclo[2.2.1]heptane Derivatives

The invention is a method for producing bicyclo[2.2.1] heptane derivatives represented by the formula (VII) by dimerization of materials that are methylene group and bicyclo[2.2.1]heptane ring compounds with a substituted methyl group and/or bicyclo[2.2.1]heptene ring compounds with a substituted methyl group under 60° C. in the presence of acid catalyst and hydrogenating the produced dimer under 200–300° C. in the presence of hydrogenating catalyst.

In the formula, the methylene group and bicyclo[2.2.1] heptane ring compounds, substituted methylene group and with methyl group, are exemplified by 2-methylene-3-methylbicyclo[2.2.1]heptane, 3-methylene-2-methylbicyclo [2.2.1]heptane, 2-methylene-7-methylbicyclo[2.2.1] heptane, 3-methylene-7-methylbicyclo[2.2.1]heptane, 2-methylene-5-methylbicyclo[2.2.1]heptane, 3-methylene-5-methylbicyclo[2.2.1]heptane, 2-methylene-6-methylbicyclo[2.2.1]heptane, 3-methylene-6-methylbicyclo [2.2.1]heptane, 2-methylene-1-methylbicyclo[2.2.1] heptane, 3-methylene-1-methylbicyclo[2.2.1]heptane, 2-methylene-4-methylbicyclo[2.2.1]heptane, 3-methylene-4-methylbicyclo[2.2.1]heptane, 2-methylene-3,7-dimethylbicyclo[2.2.1]heptane, 3-methylene-2,7-dimethylbicyclo[2.2.1]heptane, 2-methylene-3,6-dimethylbicyclo[2.2.1]heptane, 3-methylene-2,6-dimethylbicyclo[2.2.1]heptane, 2-methylene-3,3-dimethylbicyclo[2.2.1]heptane, 3-methylene-2,2-dimethylbicyclo[2.2.1]heptane.

Among them, 2-methylene-3-methylbicyclo[2.2.1] heptane is preferable in the presence of exo-3-methyl-2-methylenebicyclo[2.2.1]heptane and endo-3-methyl-2-methylenebicyclo[2.2.1]heptane and 3-methylene-2-methylbicyclo[2.2.1]heptane in the presence of exo-2-methyl-3-methylenebicyclo[2.2.1]heptane and endo-2-methyl-3-methylenebicyclo[2.2.1]heptane.

On the other hand, the bicyclo[2.2.1]heptene ring compounds with substituted methyl group are exemplified by 2,3-dimethylbicyclo[2.2.1]hepto-2-ene, 2,7-dimethylbicyclo[2.2.1]hepto-2-ene, 2,5-dimethylbicyclo [2.2.1]hepto-2-ene, 2,6-dimethylbicyclo[2.2.1]hepto-2-ene, 1,2-dimethylbicyclo[2.2.1]hepto-2-ene, 2,4-dimethylbicyclo[2.2.1]hepto-2-ene, 2,3,7-trimethylbicyclo [2.2.1]hepto-2-ene, 2,3,6-trimethylbicyclo[2.2.1]hepto-2-ene, etc.

Among them, 2,3-dimethylbicyclo[2.2.1]hepto-2-ene is preferable.

For the purpose of producing bicyclo[2.2.1]heptane derivatives having the stereochemical structure represented by said formulae from (I) to (VI), the mixture of 2-methylene-3-methylbicyclo[2.2.1]heptane, 3-methylene-2-methylbicyclo[2.2.1]heptane, and 2,3-dimethylbicyclo{2.2.1}hepto-2-ene is preferably used as material olefin.

In the invention, said material olefin is first dimerized in the presence of acid catalyst. A compound, either inorganic acid or organic acid, showing acid property can be used as the acid catalyst. Besides, concerning the form of the acid catalyst, either liquid or solid can be used. Preferable acid catalyst is exemplified by hydrofluoric acid, mineral acids such as polyphosphoric acids, organic acids such as triflic acid, lewis acids such as aluminium chloride, ferric chloride, tin tetrachloride, titanium tetrachloride, boron trifluoride, a complex of boron trifluoride, boron tribromide, aluminium bromide, gallium chloride, and gallium bromide, and organic aluminium compounds such as triethyl aluminium, diethyl aluminium chloride, and diethyl aluminium dichloride, etc.

Among these acid catalysts, such Lewis acids as boron trifluoride, a complex of boron trifluoride, tin tetrachloride, titanium tetrachloride, and aluminium chloride. Among them, such complexes of boron trifluoride as diethyl ether complex of boric trifluoride, water complex of boron trifluoride, and alcohol complex of boron trifluoride are further preferable in the point of possible dimerization under lower temperature.

The production of bicyclo[2.2.1]heptane derivatives having a stereochemical structure represented by said formulae from (I) to (VI) can be preferably carried out by using diethyl ether complex of boron trifluoride as catalyst for dimerization.

Concerning amounts used for these catalysts, there is no special restriction, however, usually, 0.1–100 weight percent in proportion to material olefin, preferably around 0.5–20 weight percent.

In the dimerization reaction, the solvent is not always used for, however, the solvent may be used for handling of material olefin at reaction time or regulating the progress of the reaction. Preferable catalysts are exemplified by saturated hydrocarbons such as various pentanes, various hexanes, various octanes, various nonanes, various decanes, etc., alicyclic hydrocarbons such as cyclopentane, cyclohexane, methylcyclosane, decalin, etc., ether compounds such as diethyl ether, tetrahydrofuran, etc., compounds containing halogens such as methylene chloride, dichloroethane, etc., and nitro compounds such as nitromethane, nitrobenzene, etc.

The dimerization reaction is usually carried out under reaction temperature of 60° C. or lower, preferably 40° C. or lower. A reaction temperature over 60° C. allows isomerization of the dimer produced by the reaction. The target bicyclo[2.2.1]heptane derivative of a stereochemical structure is preferably yielded with a high purity by the reaction of dimerization under lower temperature, because a plurality of stereochemical isomers produced by isomerization reaction is difficult to separate. The lower limit temperature is not restricted, when the dimerization reaction is going well; however, −70° C. or higher temperature is economically preferable and −30° C. or higher temperature is further preferable.

The reaction pressure of dimerization reaction is determined to an appropriate range according to reaction temperature, kind of catalyst, presence or absence of solvent, and kind of solvent; however, an ordinary pressure is usually preferable. In addition, reaction time is preferably in the range of 0.5–10 hours usually.

In the invention, the dimer of the material olefin obtained by such conditions is usually hydrogenated in the presence of catalyst for hydrogenation.

Support of the catalyst for hydrogenation usually compounded with a metal component can be used. Preferably, an example is a catalyst in which a metal component of an element such as nickel, ruthenium, palladium, platinum, rhodium, and iridium of VIII group of the periodic table is contained in inorganic oxide support such as diatomite, alumina, silica alumina, and activated clay. Among them, nickel catalyst such as nickel/diatomite, nickel/silica alumina, etc. is preferable in the point of economy and possible selection of product. Besides, such solid acid as zeolite, silica alumina, and activated clay as a promoter for hydrogenation may be used, if necessary.

For reference, the production of bicyclo[2.2.1]heptane derivatives having a stereochemical structure that is represented by the formulae from (I) to (VI) is preferably carried out using nickel/diatomite catalyst as catalyst for hydrogenation.

The amount of catalyst used is usually 0.1–100 weight percent in the proportion to said dimerized product, preferably 1–20 weight percent.

On the other hand, hydrogenation reaction goes without any solvent as same as said dimerization reaction; however, solvent is preferably used and preferable solvent is exemplified by saturated hydrocarbons such as various pentanes, various hexanes, various octanes, various nonanes, various decanes, etc., alicyclic hydrocarbons such as cyclo pentane, cyclohexane, methylcyclosane, decalin, etc.

The reaction temperature for the hydrogenation reaction is preferably 200–300° C. and further preferably 220–280° C. The reaction temperature lower than 200° C. may insufficiently decrease the viscosity of the product by isomerization and may insufficiently increase the viscosity index. On the other hand, the temperature higher than 300° C. may lower the yield by decomposition of the product.

Furthermore, a reaction pressure is not specially restricted usually to allow an ordinary pressure to 200 kg/cm² G, preferably an ordinary pressure to 100 kg/cm² G. Hydrogen pressure is preferably in 5–90 kg/cm² G, further preferably 10–80 kg/cm² G. Reaction time is usually 1–10 hours.

Bicyclo[2.2.1]heptane derivatives represented by said formula (VII) and yielded under such conditions show a high traction coefficient under high temperature and an excellent characteristic of viscosity under low temperature to allow to use as a CVT oil for traction drive in the world from cold and tropical regions.

3. Fluid for Traction Drive

The fluid for traction drive of the invention was obtained on the basis of a finding that said bicyclo[2.2.1]heptane derivatives, particularly bicyclo[2.2.1]heptane derivatives having a stereochemical structure represented by the formulae from (I) to (IV), have excellent physical properties as the fluid for traction drive.

The fluid for traction drive of the invention is consisted of a synthetic oil having physical properties of the following (1) to (6).

(1) The number-average molecular weight of a compound contained in a synthetic oil is 210 or more, preferably 215~290. The number-average molecular weight less than 210 may cause an increase in a volatilized amount of the fluid for traction drive in the use under high temperature.

(2) A kinematic viscosity of a synthetic oil at 40° C. is 10–25 mm²/s, preferably 12–24 mm²/s. The kinematic viscosity of synthetic oil at 40° C. is less than 10 mm²/s may cause low viscosity under high temperature to result in an insufficient thickness of the layer of a lubricating oil. On the other hand, the kinematic viscosity at 40° C. exceeds 25 mm²/s may cause the low temperature viscosity exceeding 150000 mPa·s under −40° C.

(3) A viscosity index of synthetic oil is 60 or higher, preferably 65 or higher. The index less than 60 may cause the low temperature viscosity exceeding 15000 Pa·s under −40° C.

(4) Pour point of synthetic oil is under −40° C., preferably under −45° C. The pour point higher than −40° C. causes difficulty of starting the traction drive machine in the use in cold region.

(5) The density of synthetic oil under 20° C. is higher than 0.93 g/cm³, preferably in the range from 0.93 to 1.50 g/cm³. The density less than 0.93 g/cm³ is not preferable due to the occurrence of lower traction coefficient under 140° C.

(6) The traction coefficient of synthetic oil under the temperature of 140° C. is 90% or higher of that of 2,4-dicyclohexyl-2-methylpentane, preferably that of 2,4-dicyclohexyl-2-methylpentane. The coefficient less than 90% of that of 2,4-dicyclohexyl-2-methylpentane may cause insufficient capacity of torque transmission under 140° C.

A compound consisting of the synthetic oil of the invention meeting the physical properties of said (1) to (6) is not specially restricted; however, preferable compounds are exemplified by hydrogenated diner of at least one alicyclic compound selected from groups including bicyclo[2.2.1]heptane ring compounds, bicyclo[3.2.1]octane ring compounds, and bicyclo[2.2.2]octane ring compounds.

Among these compounds, further preferable is hydrogenated diner of bicyclo[2.2.1]heptane ring compounds represented by the following formula (VIII).

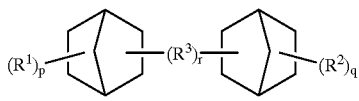

(VIII)

(In the formula, both $R^1$ and $R^2$ represent hydrogen atoms or alkyl groups with carbon numbers of 1–3, $R^3$ represents methylene group, ethylene group, or trimethylene group that may be substituted by methyl group or ethyl group in a side chain, r represents 0 or 1, both p and q represent integral numbers of 1–3).

Bicyclo[2.2.1]heptane derivatives represented by the following formula (VII),

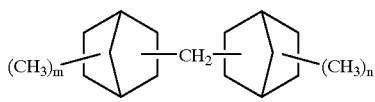

(VII)

particularly, bicyclo[2.2.1]heptane derivatives having a stereochemical structure represented by the following formula (I) to (VI) are preferable.

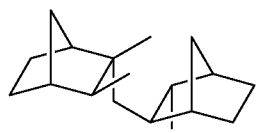

(I)

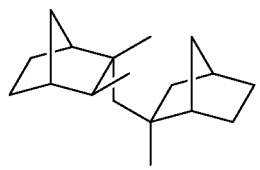

(II)

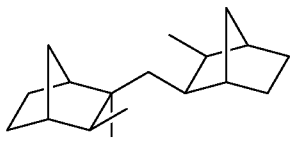

(III)

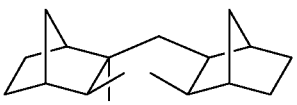

(IV)

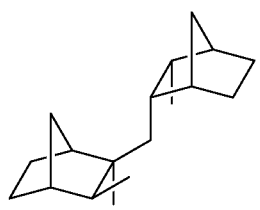

(V)

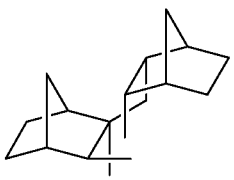

(VI)

(In the formula, m represents 2 or 2 and n represents 1 or 2).

Said hydrogenated compounds can be used as a single compound or a mixture of two or more compounds. Hydrogenated compounds represented by said formulae (VIII) can be prepared by dimerization, hydrogenating, and distillation of the material olefinic alicyclic compound.

The material olefinic alicyclic compound is exemplified by bicyclo[2.2.1]hept-2-ene, alkenyl-substituted bicyclo[2.2.1]hept-2-ene such as vinyl-substituted or isopropenyl-substituted bicyclo[2.2.1]hept-2-ene, a alkylidene-substituted bicyclo[2.2.1]hept-2-ene such as methylene-substituted, ethylidene-substituted, or isopropylidene-substituted bicyclo[2.2.1]hept-2-ene, alkenyl-substituted bicyclo[2.2.1]heptane such as vinyl-substituted or isopropenyl-substituted bicyclo[2.2.1]heptane, alkylidene-substituted bicyclo[2.2.1]heptane such as methylene-substituted, ethylidene-substituted or isopropylidene-substituted bicyclo[2.2.1]heptane, bicyclo[3.2.1]octene, alkenyl-substituted bicyclo[3.2.1]octene such as vinyl-substituted or isopropenyl-substituted bicyclo[3.2.1]octene, alkylidene-substituted bicyclo[3.2.1]octene such as methylene-substituted, ethylidene-substituted, or isopropylidene-substituted bicyclo[3.2.1]octene, alkenyl-substituted bicyclo[3.2.1]octane such as vinyl-substituted or isopropenyl-substituted bicyclo[3.2.1]octane, alkylidene-substituted bicyclo[3.2.1]octane such as methylene-substituted, ethylidene-substituted, or isopropylidene-substituted bicyclo[3.2.1]octane, bicyclo[3.3.0]octene, alkenyl-substituted bicyclo[3.3.0]octene such as vinyl-substituted or isopropenyl-substituted bicyclo[3.3.0]octene, alkylidene-substituted bicyclo[3.3.0]octene such as methylene-substituted, ethylidene-substituted, or isopropylidene-substituted bicyclo[3.3.0]octene, alkenyl-substituted bicyclo[3.3.0]octane such as vinyl-substituted or isopropenyl-substituted bicyclo[3.3.0]octane, alkylidene-substituted bicyclo[3.3.0]octane such as methylene-substituted, ethylidene-substituted, or isopropylidene-substituted bicyclo[3.3.0]octane, bicyclo[2.2.2]octene, alkenyl-substituted bicyclo[2.2.2]octene such as vinyl-substituted or isopropenyl-substituted bicyclo[2.2.2]octene, alkylidene-substituted bicyclo[2.2.2]octene such as methylene-substituted, ethylidene-substituted, or isopropylidene-substituted bicyclo[2.2.2]octene, alkenyl-substituted bicyclo[2.2.2]octane such as vinyl-substituted or isopropenyl-substituted bicyclo[2.2.2]octane, alkylidene-substituted bicyclo[2.2.2]octane such as methylene-substituted, ethylidene-substituted, or isopropylidene-substituted bicyclo[2.2.2]octane.

Among them, appropriate material alicyclic compounds preferable as a synthetic oil, represented by said formula (VIII), and yielding hydrogenated dimer of bicyclo[2.2.1] heptane ring compounds for use are exemplified by bicyclo[2.2.1]hept-2-ene; 2-methylenebicyclo[2.2.1]heptane; 2-methylbicyclo[2.2.1]hept-2-ene; 2-methylene-3-methylbicyclo[2.2.1]heptane; 2,3-dimethylbicyclo[2.2.1] hept-2-ene; 2-methylene-7-methylbicyclo[2.2.1]heptane; 2.7-dimethylbicyclo[2.2.1]hept-2-ene; 2-methylene-5- methylbicyclo[2.2.1]heptane; 2,5-dimethylbicyclo[2.2.1]hept-2-ene; 2-methylene-6-methylbicyclo[2.2.1]heptane; 2,6-dimethylbicyclo[2.2.1]hept-2-ene; 2-methyl-1-methylbicyclo[2.2.1]heptane; 1,2-dimethylbicyclo[2.2.1]hepto-2-ene; 2-methylene-4-methylbicyclo[2.2.1]heptane; 2,4-dimethylbicyclo[2.2.1]hepto-2-ene; 2-methylene-3.7-dimethylbicyclo[2.2.1]heptane; 2,3,7-trimethylbicyclo[2.2.1]hept-2-ene; 2-methylene-3.6-dimethylbicyclo[2.2.1]heptane; 2-methylene-3.3-dimethylbicyclo[2.2.1]heptane; 2,3,6-trimethylbicyclo[2.2.1]hept-2-ene; 2-methylene-3-ethylbicyclo[2.2.1]heptane; 2-methyl-3-ethylbicyclo[2.2.1]hept-2-ene.

Said dimerization means not only the dimerization of same olefins, but also the dimerization of plural different olefins.

The dimerization reaction of said olefinic alicyclic ring compounds is carried out by adding solvent, if necessary, in the presence of catalyst.

The catalyst used for the dimeriztion reaction is, usually, acid catalyst. Individual catalyst can be same as that used for the production of bicyclo[2.2.1]heptane derivatives represented by said following formula (VII) and its detailed description is omitted here. In addition, the amount of used catalyst and the condition of reaction are also same and its detailed description is omitted here.

In the invention, the dimer yielded is hydrogenated. The condition of hydrogenating treatment and other conditions are same as those used for the production of bicyclo[2.2.1]heptane derivatives represented by said formula (VII) and its detailed description is omitted here.

In the invention, the synthetic oil having physical properties of said (1)–(6) is used for base oil of the fluid for traction drive, however, other liquid matter may be mixed with the synthetic oil for use in the range within the range of the physical properties of said (1)–(6). For example, such base oil with low viscosity as poly α-olefin oil (PAO) and diester can be mixed to keep a traction coefficient under high temperature and such base material as the base oil of alicyclic compound for traction and hydrogenated dicyclopentadiene petroleum resin, etc., to keep a viscosity under low temperature can be mixed to improve a traction coefficient under a high temperature. Mixing amount for addition of other liquid matter is preferably 15 weight percent or less.

In the use for the fluid for traction drive, the base oil with said synthetic oil as a main component is compounded with such additives as antioxidant, rust inhibitor, detergent dispersant, pour point depressant, an viscosity index improver, extreme pressure agent, anti-water agent, oiliness agent, antifoaming agent, corrosion inhibitor, etc., in suitable amount if necessary.

EXAMPLES

Examples of the invention are separately given below, however, the following embodiment is to be considered in all respects as illustrative and not restrictive.

Example 1
Production of Material Olefin

Crotonaldehyde (561 g=8 mol) and bicyclopentadiene (352 g=2.67 mol) were put in 2 L, stainless steel-made autoclave to react by mixing for 3 hours under 170° C. The reaction solution was cooled to a room temperature, 18 g of a Raney nickel catalyst (Kawaken Fine Chemicals, K.K. made, M-300T) was added, and finally, hydrogenation was carried out under a hydrogen pressure of 9 kg/ cm2 G and reaction temperature of 150° C. for 4 hours. After cooling, the catalyst was filtered to separate, the filtrate was distilled under a reduced pressure to yield 565 g of fraction under 105° C./20 mm Hg. The result of mass spectrum analysis and nuclear magnetic resonance spectrum analysis of the fraction showed that the fraction is 2-hydroxymethyl-3-methylbicyclo[2.2.1]heptane and 3-hydroxymethyl-2-methylbicyclo[2.2.1]heptane.

Next, 20 g of γ-alumina [Nikki Kagaku, K.K. made, N612N] was put in a quartz glass-made flow reaction tube under an atmospheric pressure, with an outer diameter of 20 mm and a length of 500 mm to start dehydration reaction going under a reaction temperature of 285° C. and weight hourly space velocity (WHSV)=1.1 hr$^{-1}$ and finally, 450 g of the dehydrated reaction product of 2-hydroxymethyl-3-methylbicyclo[2.2.1]heptane and 3-hydroxymethyl-2-methylbicyclo[2.2.1]heptane was yielded containing 55 weight percent of 2-methylene-3-methylbicyclo[2.2.1]heptane and 3-methylene-2-methylbicyclo[2.2.1]heptane and 30 weight percent of 2,3-dimethylbicyclo[2.2.1]hept-2-ene.

Production of Hydrogenated Dimer

Diethyl ether complex (8 g) of boron trifluoride and the olefin compound (400 g) yielded from said steps were put in a 1-L four-neck flask and stirred under 20° C. for 4 hours by using a mechanical stirrer to start dimerization reaction going. The reaction mixture was washed with diluted NaOH aqueous solution and saturated brine, 12 g of nickel/diatomite catalyst [Nikki Kagaku, K.K. made, N-113] for hydrogenation was added in a 1-L autoclave, and finally, hydrogenating reaction was started under the condition of 30 kg/cm$^2$ G of hydrogen pressure, reaction temperature of 250° C., and reaction time of 6 hours. After the completion of the reaction, the catalyst was removed by filtration and the filtrate was distilled under a reduced pressure to yield 240 g of a target hydrogenated dimer. Table 1 shows the measured result of general properties and a traction coefficient of the hydrogenated dimer.

Twice rectification to separate the hydrogenated dimer was carried out to yield 1 g of a component under 149.2° C./5 mm Hg using a spinning band distillation apparatus with 120 theoretical plate number. The analysis of the component gave exo-2-methyl-exo-3-methyl-endo-2-[(endo-3-methylbicyclo[2.2.1]hepto-exo-2-yl)methyl]bicyclo[2.2.1]heptane (the compound of said formula (I)) and exo-2-methyl-exo-3-methyl-endo-2-[(endo-2-methylbicyclo[2.2.1]hept-exo-3-yl)methyl]bicyclo[2.2.1]heptane (the compound of said formula (II)) (hereafter, both these compounds are called component A) with purity of 98 weight percent.

Figure 2:
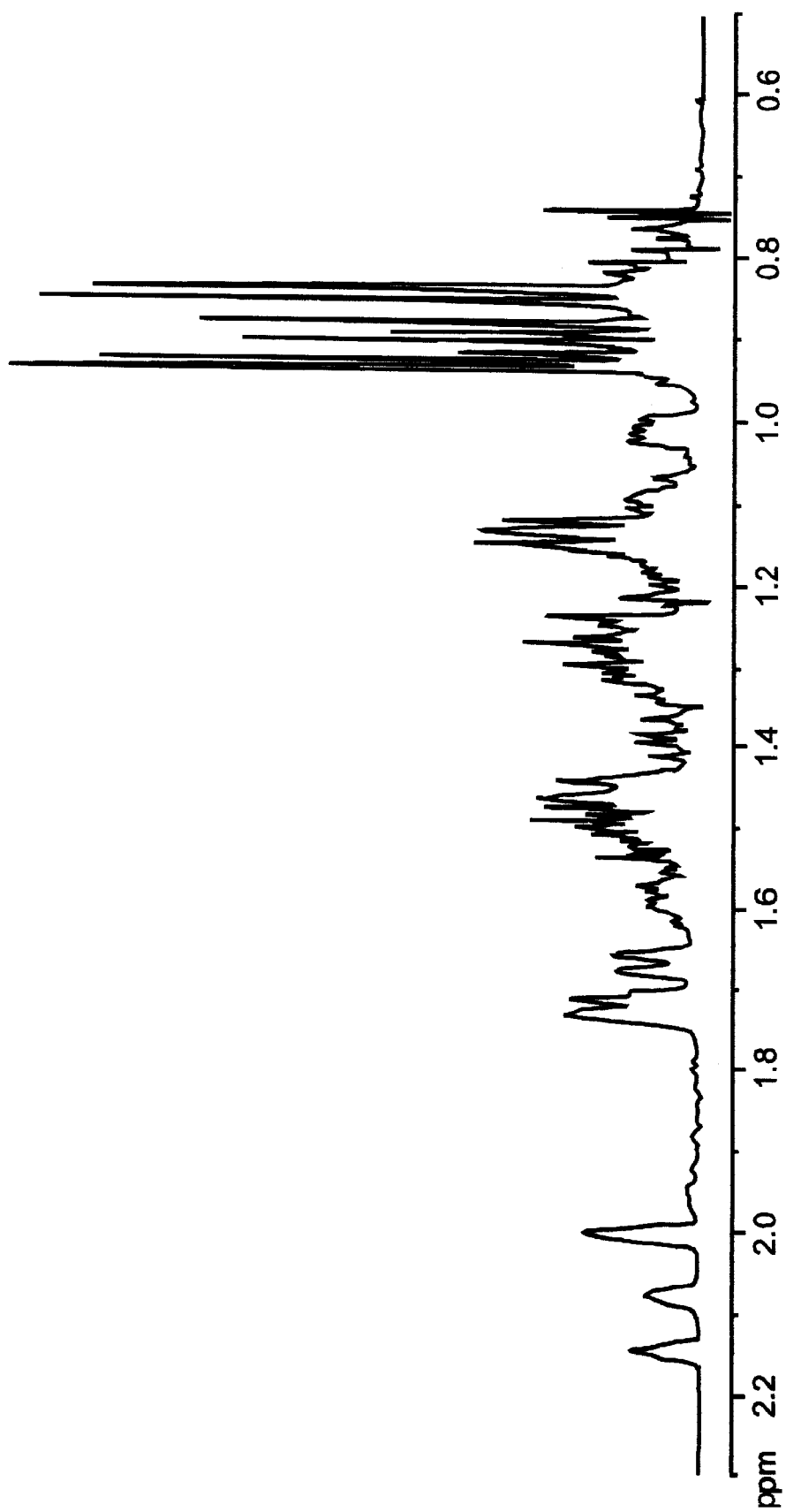
FIG. 2. $^1$H-NMR spectrogram of component A.
Figure 3:
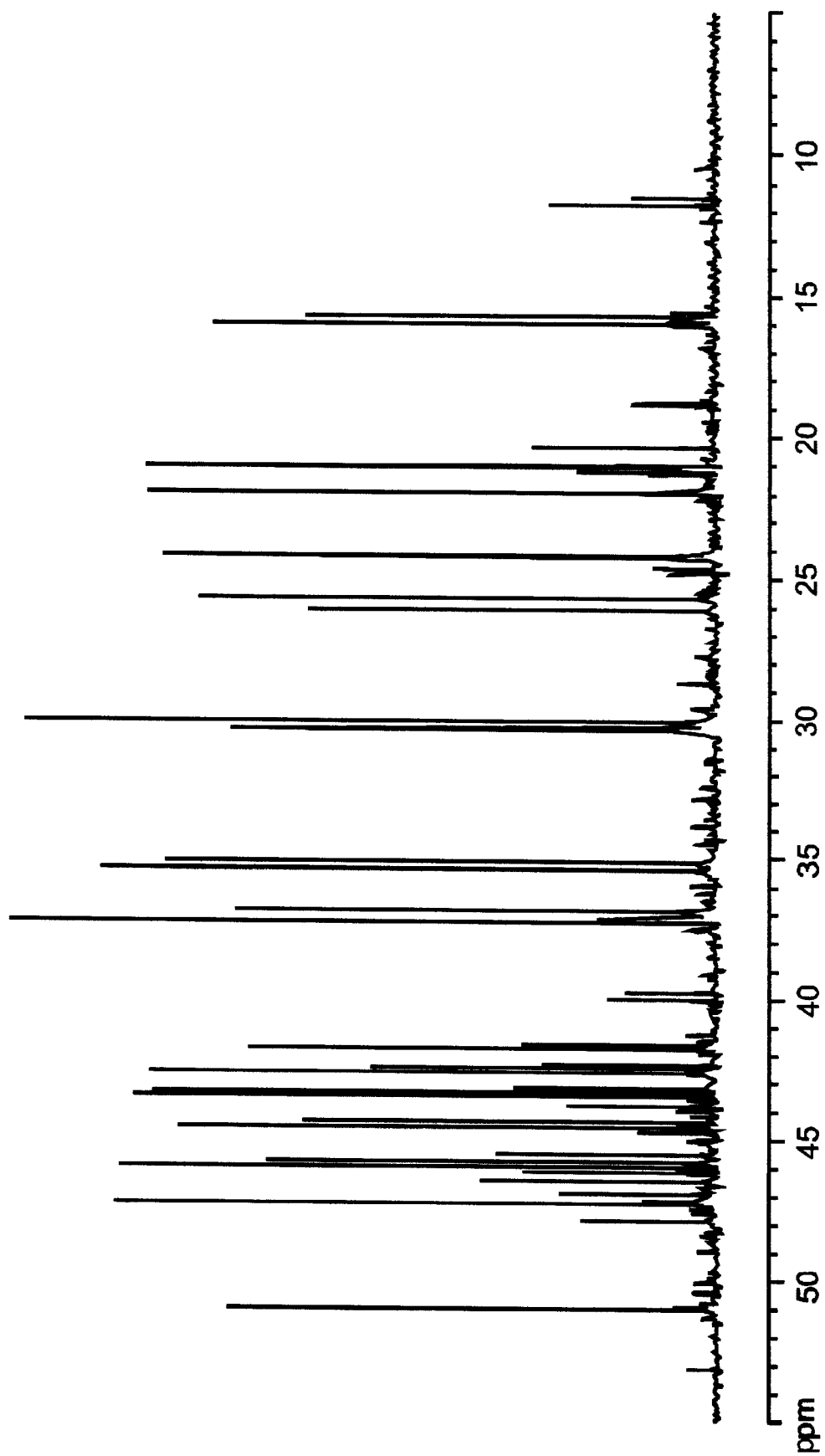
FIG. 3. $^{13}$C-NMR spectrogram of component A.
Figure 4:
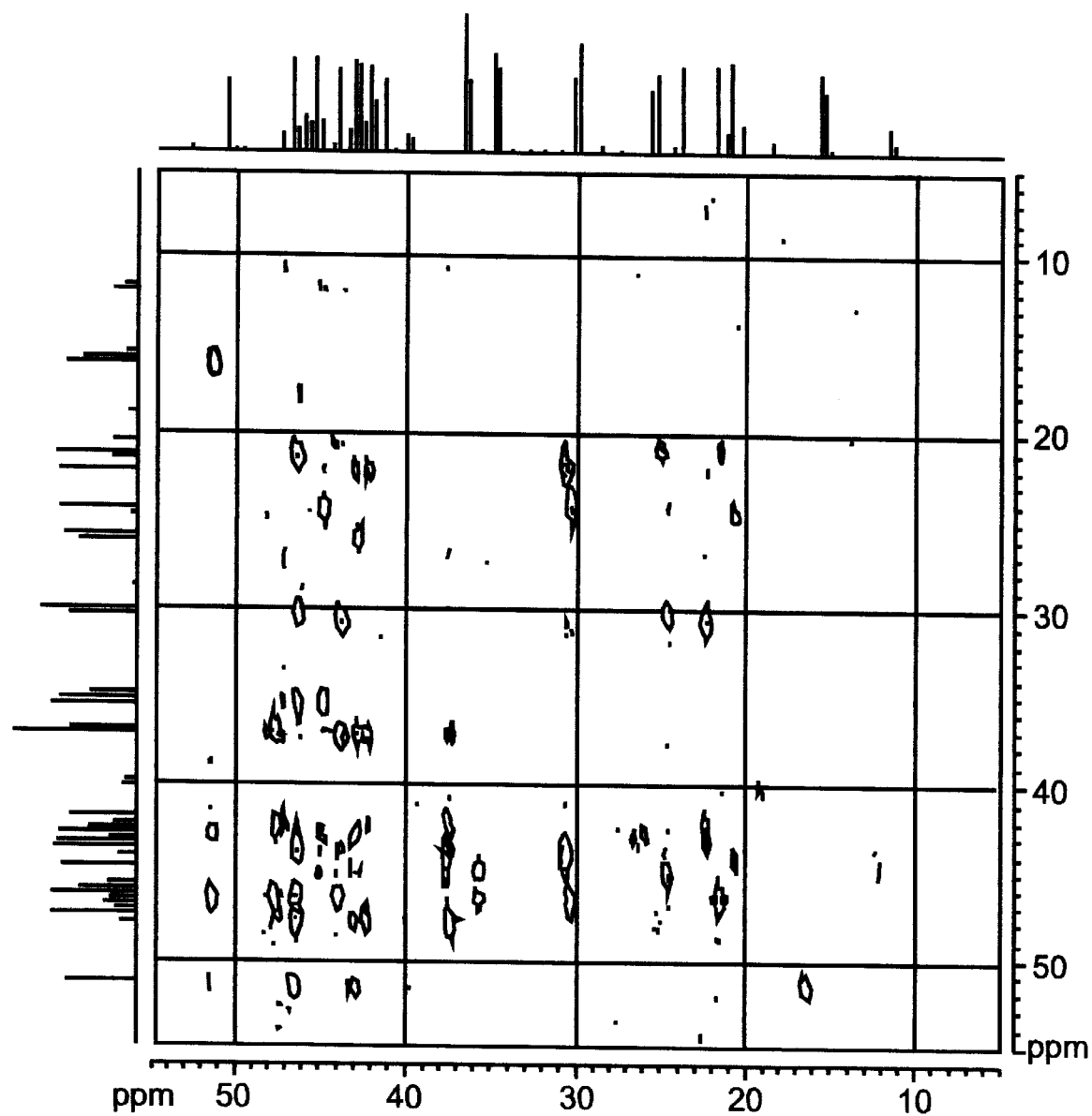
FIG. 4. $^{13}$C—$^{13}$C two-dimensional NMR spectrogram of component A.
Figure 5:
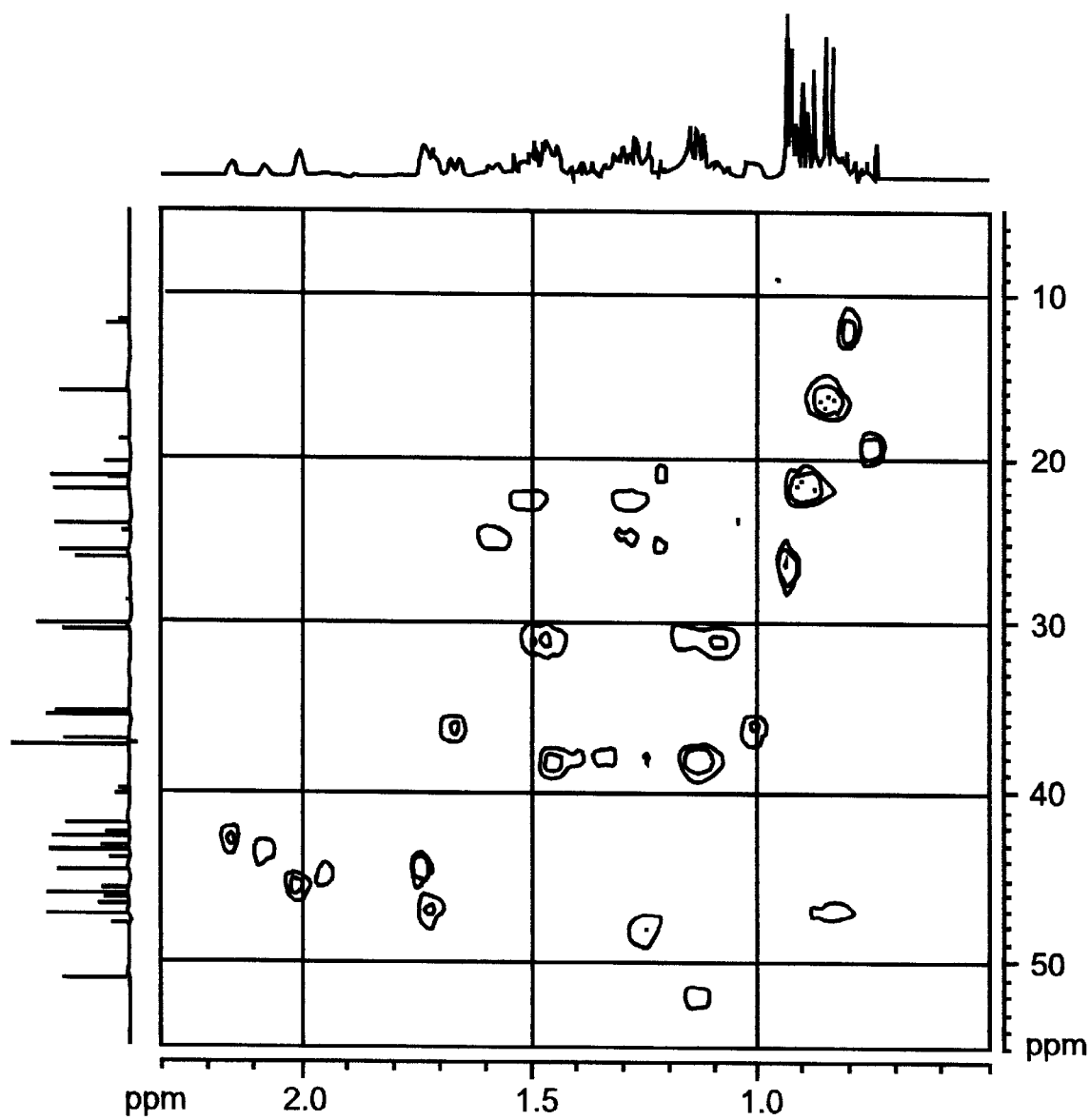
FIG. 5. $^1$H—$^{13}$C two-dimensional NMR spectrogram of component A.

FIGS. 1–5 show each spectrogram of mass chromatogram, $^1$H-NMR, $^{13}$C-NMR, $^{13}$C—$^{13}$C-NMR, and $^1$H—$^{13}$C-NMR used for structure analysis of the component A.

Besides, rectification for separation same as above yielded 1 g of a component under 133.6° C./2 mmHg. The analysis of the component showed endo-2-methyl-exo-3-methyl-exo-2-[(exo-3-methylbicyclo-[2.2.1]hept-exo-2-yl)methyl]bicyclo[2.2.1]heptane (the compound of said formula (III)) and endo-2-methyl-exo-3-methyl-exo-2-[(exo-2-methylbicyclo[2.2.1]hept-exo-3-yl)methyl]bicyclo[2.2.1]heptane (the compound of said formula (IV)) (hereafter, both these compounds are called component B) with purity of 99 weight percent.

Figure 6:
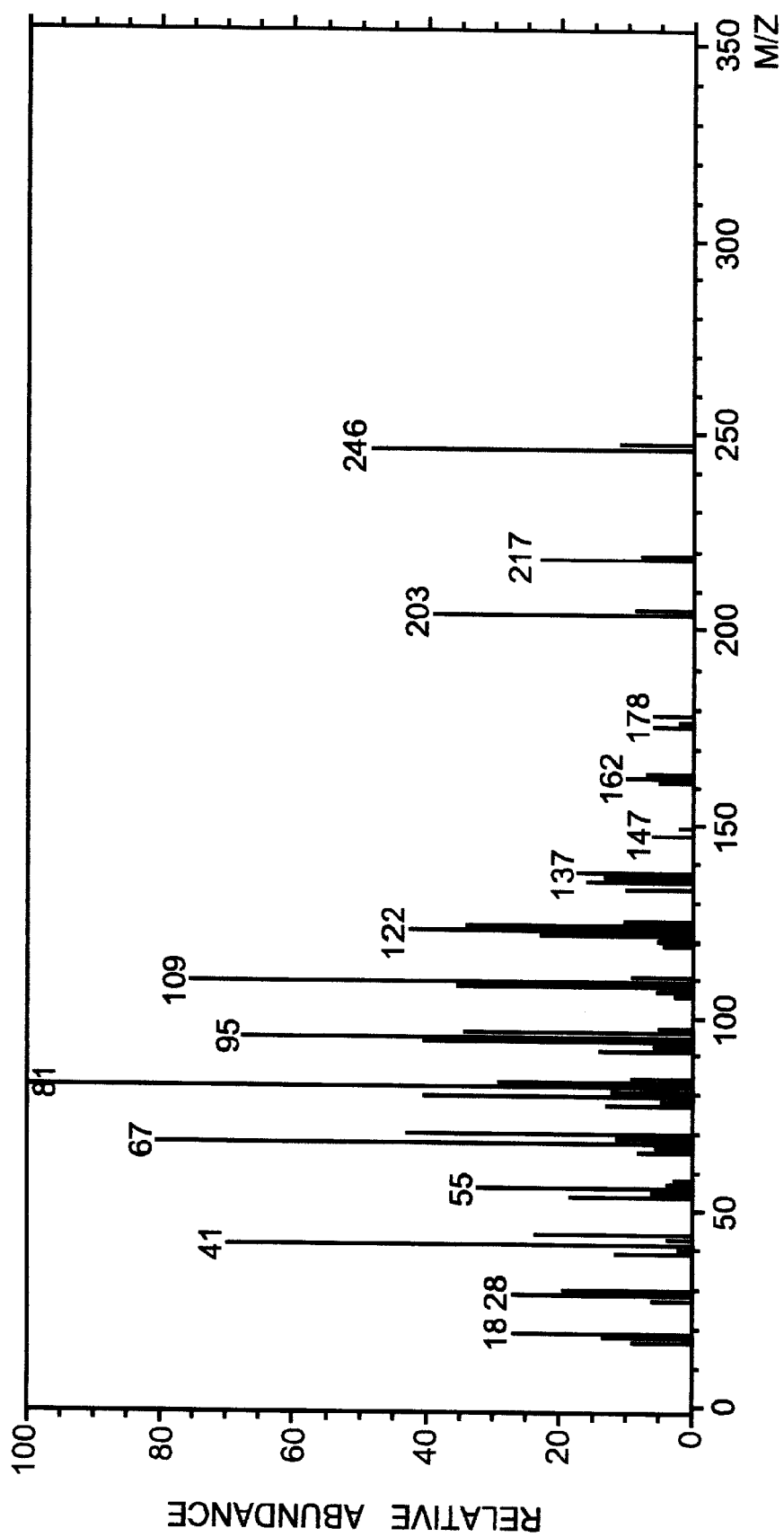
FIG. 6. A mass chromatogram of component B.
Figure 7:
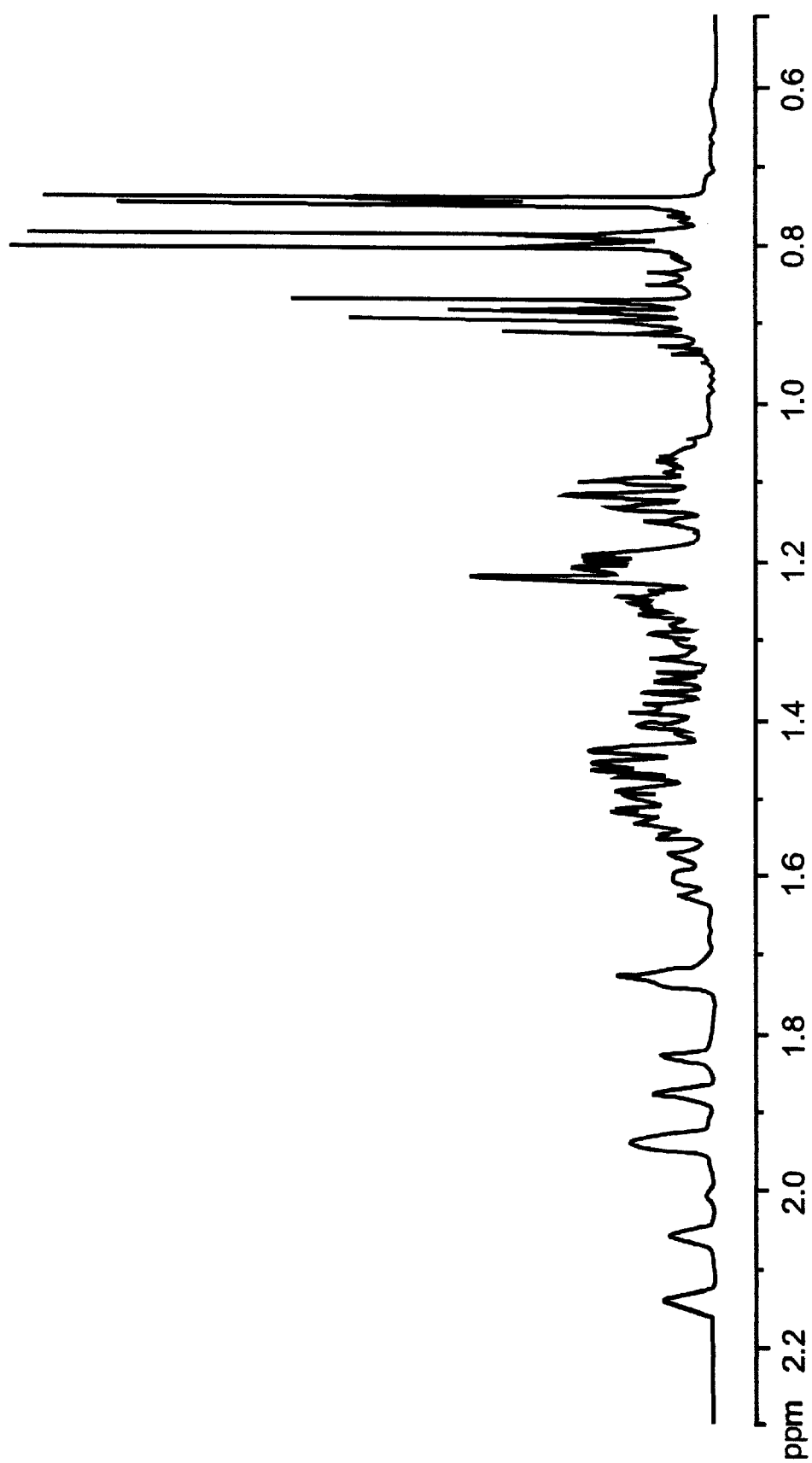
FIG. 7. $^1$H-NMR spectrogram of component B.
Figure 8:
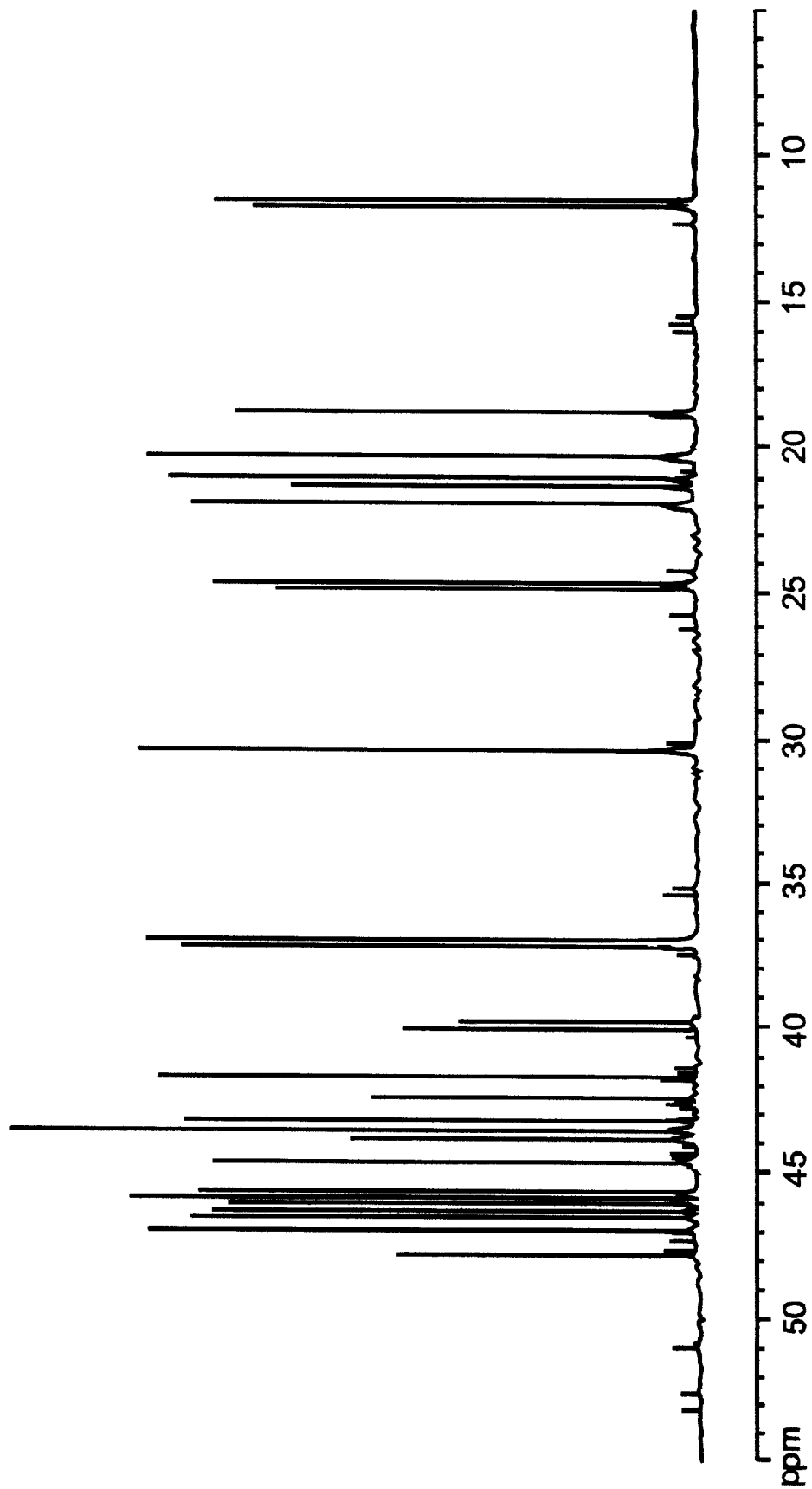
FIG. 8. $^{13}$C-NMR spectrogram of component B.
Figure 9:
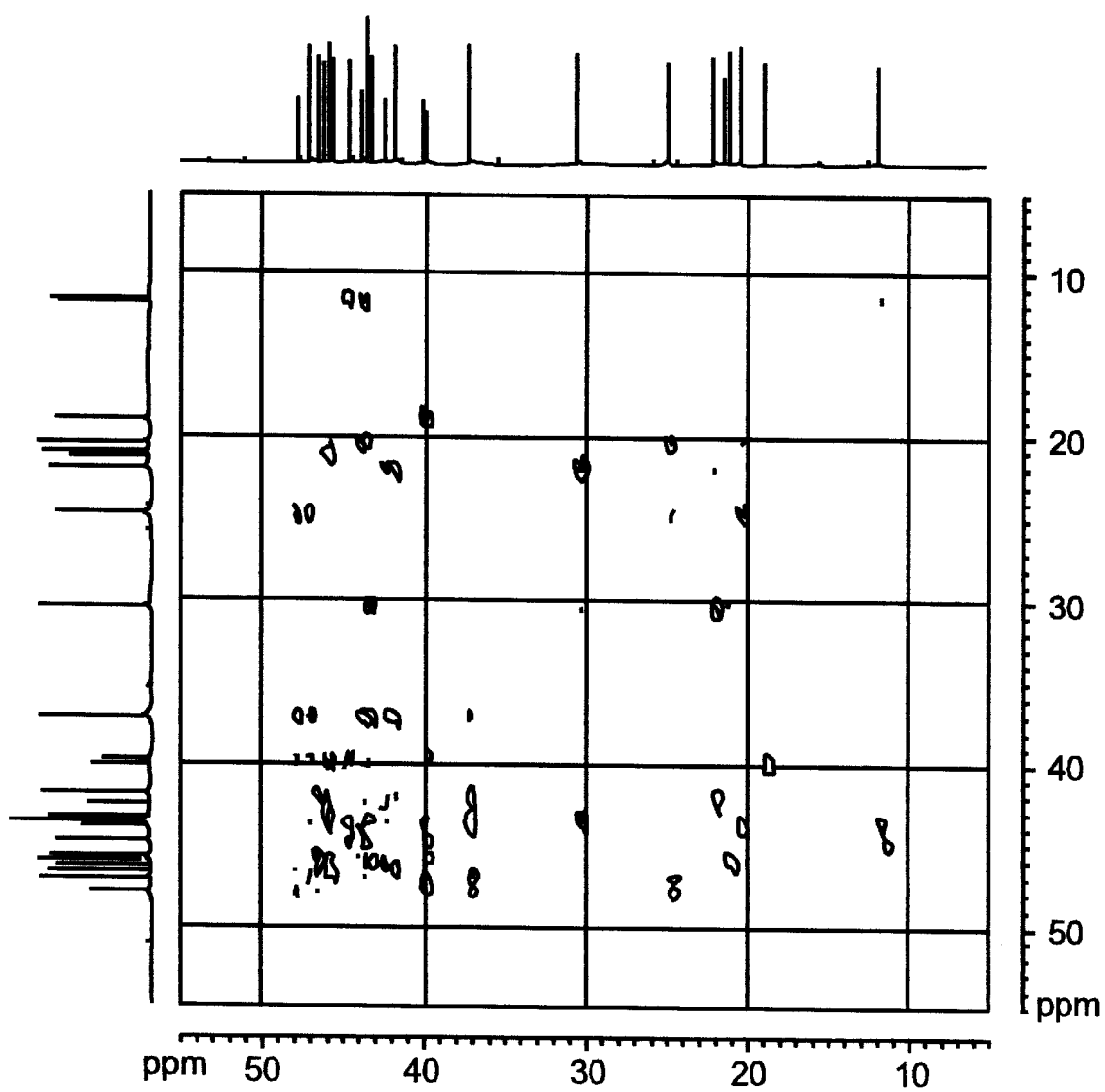
FIG. 9. $^{13}$C—$^{13}$C two-dimensional NMR spectrogram of component B.
Figure 10:
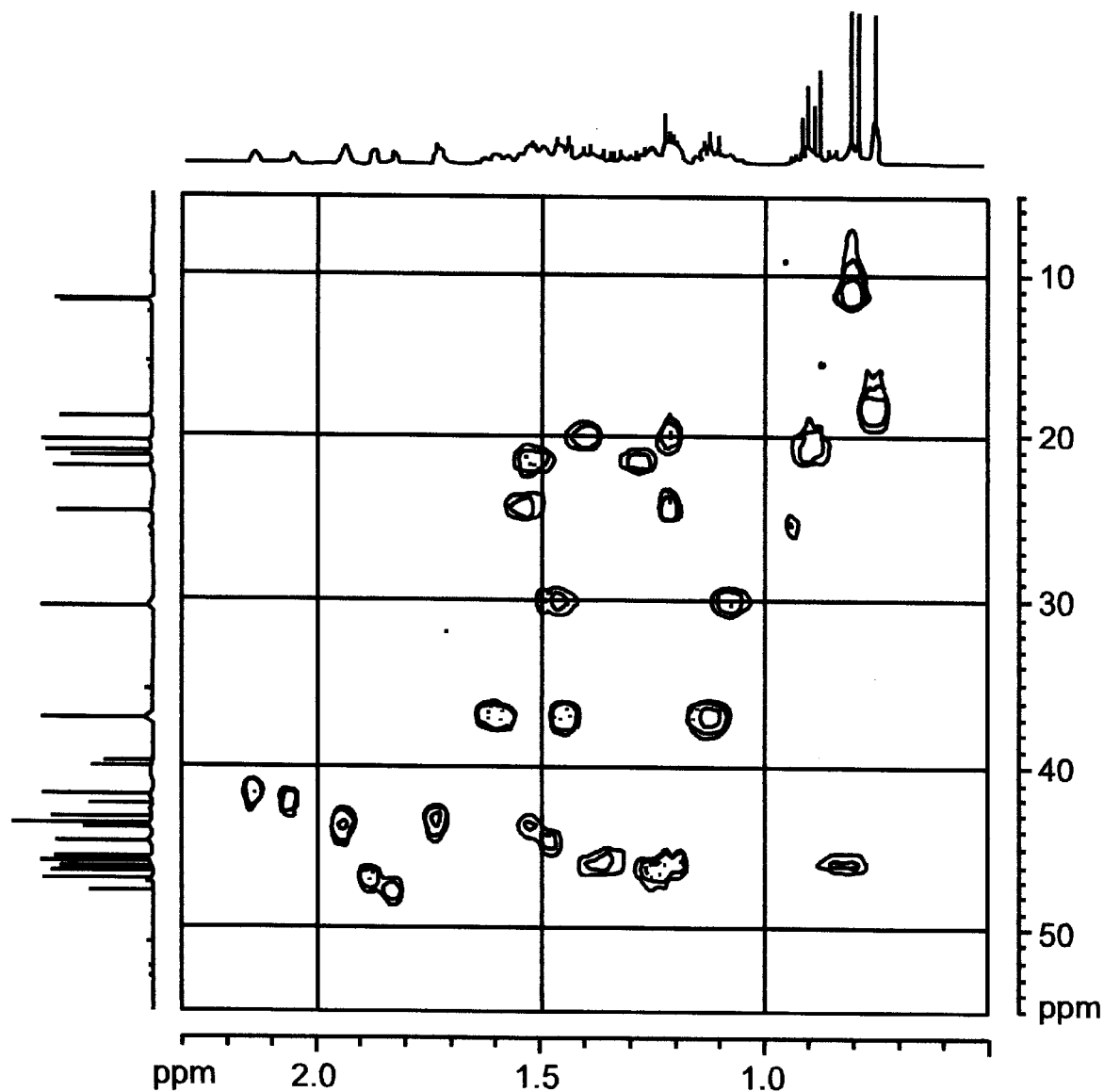
FIG. 10. $^1$H—$^{13}$C two-dimensional NMR spectrogram of component B.

FIGS. 6–10 show each spectrogram of mass chromatogram, $^1$H-NMR, $^{13}$C-NMR, $^{13}$C—$^{13}$C-NMR, and $^1$H—$^{13}$C-NMR used for structure analysis of the component B.

The result of analysis of the hydrogenated bdimer prepared in the Example 1 with gas chromatography showed contents of 20 weight percent of the component A and 60 weight percent of the component B.

Example 2

Table 1 shows the measured result of general properties and a traction coefficient of the fraction, that contains 65 weight percent of the component A and 25 weight percent of the component B, yielded by the rectification for separation of the Example 1.

Example 3

The hydrogenated dimer of 240 g was yielded by replacing the hydrogenating reaction of the Example 1 under the condition of 250° C. and 6 hours to that under 200° C. and 2 hours. Twice rectification to separate the hydrogenated dimer was carried out to yield 1 g of said component B using a spinning band distillation apparatus with 120 theoretical plate number.

Besides, rectification for separation same as above yielded 1 g of a component under 138.6° C./2 mmHg. The analysis of the component showed endo-2-methyl-exo-3-methyl-exo-2-[(endo-3-methylbicyclo-[2.2.1]hept-endo-2-yl)methyl]bicyclo[2.2.1]heptane (the compound of said formula (IV)) and endo-2-methyl-exo-3-methyl-exo-2-[(endo-2-methylbicyclo[2.2.1]hept-endo-3-yl)methyl]bicyclo [2.2.1]heptane (the compound of said formula (V)) (hereafter, both these compounds are called component C) with purity of 100 weight percent.

Figure 11:
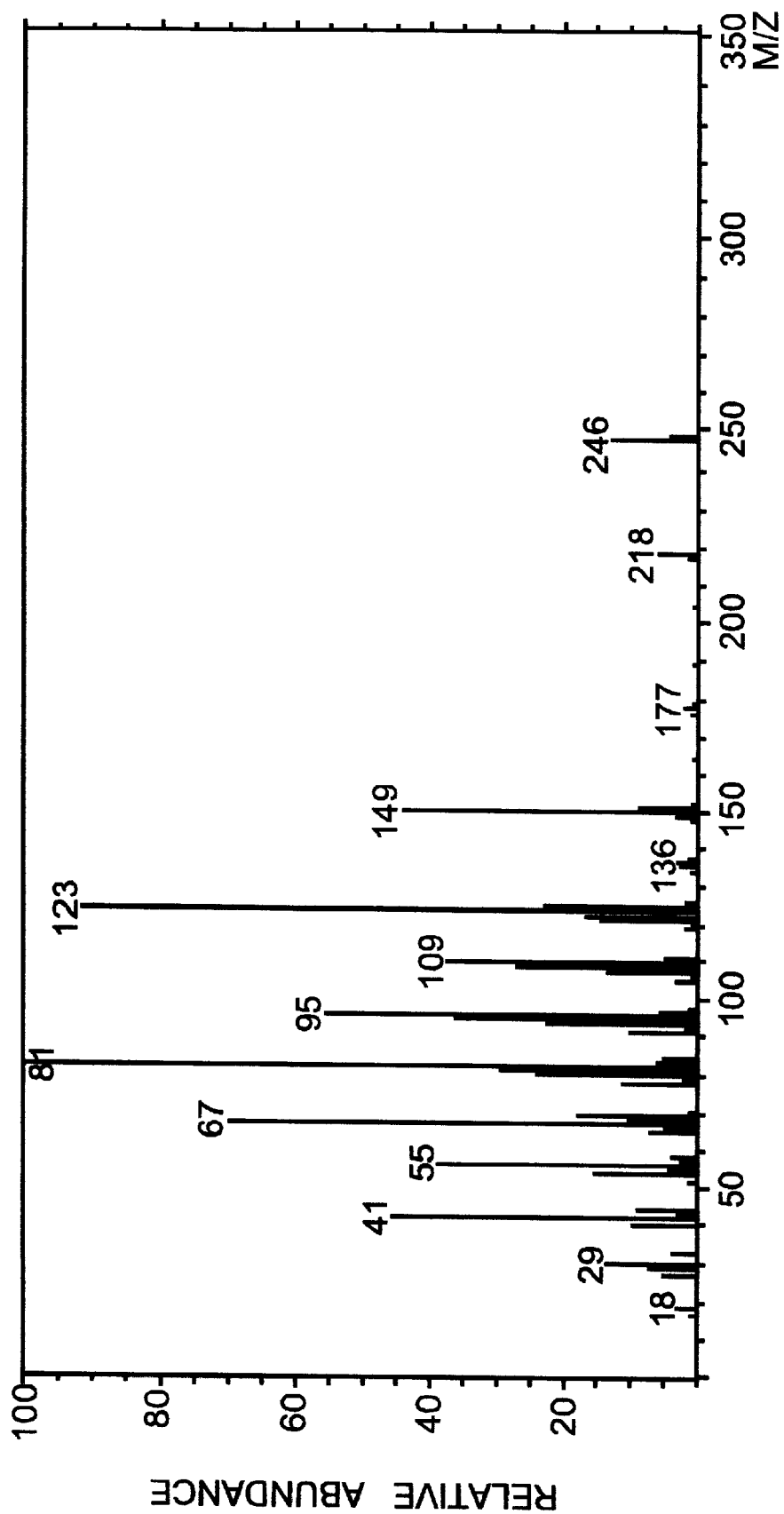
FIG. 11. A mass chromatogram of component C.
Figure 12:
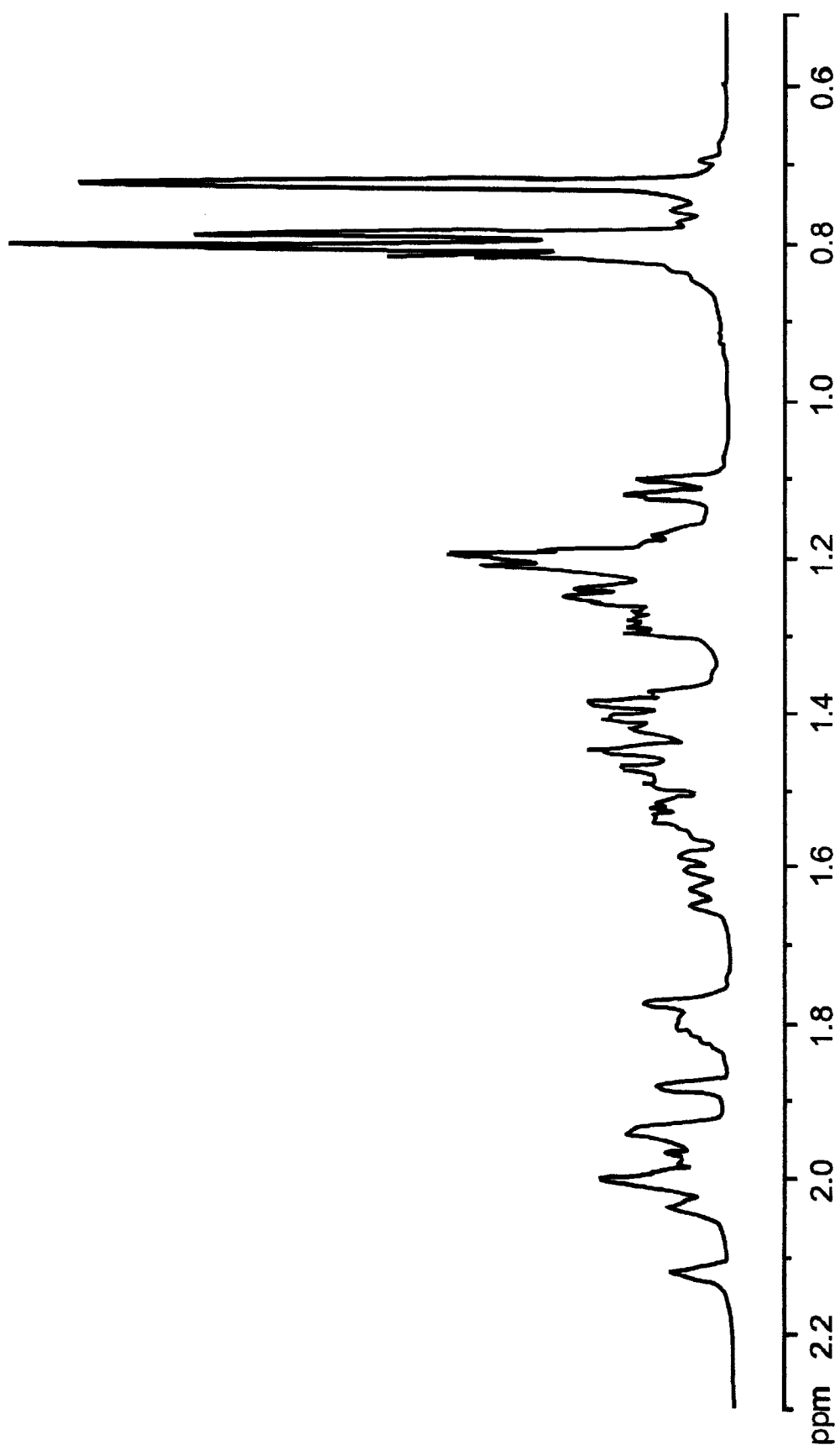
FIG. 12. $^1$H-NMR spectrogram of component C.
Figure 13:
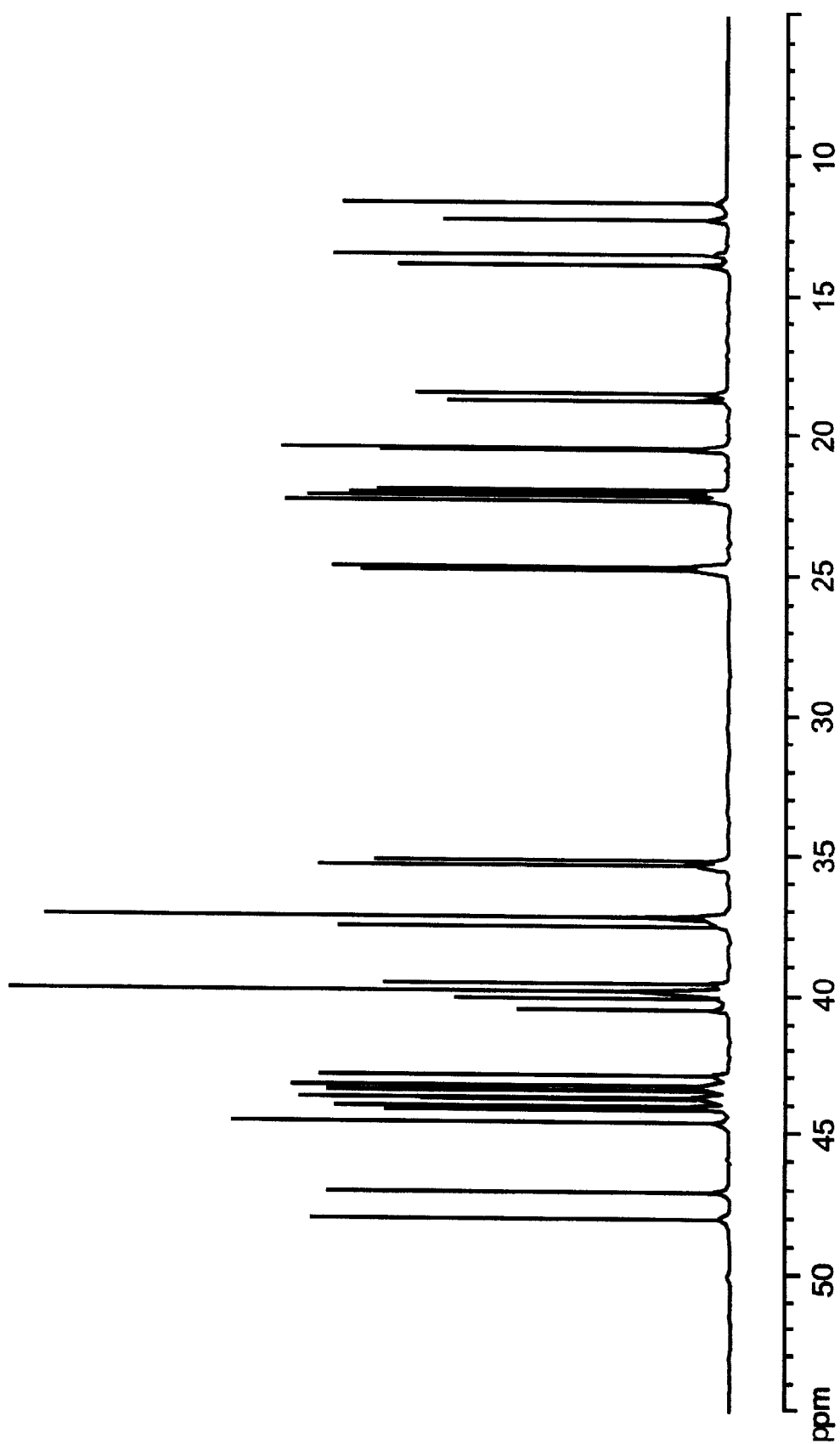
FIG. 13. $^{13}$C-NMR spectrogram of component C.
Figure 14:
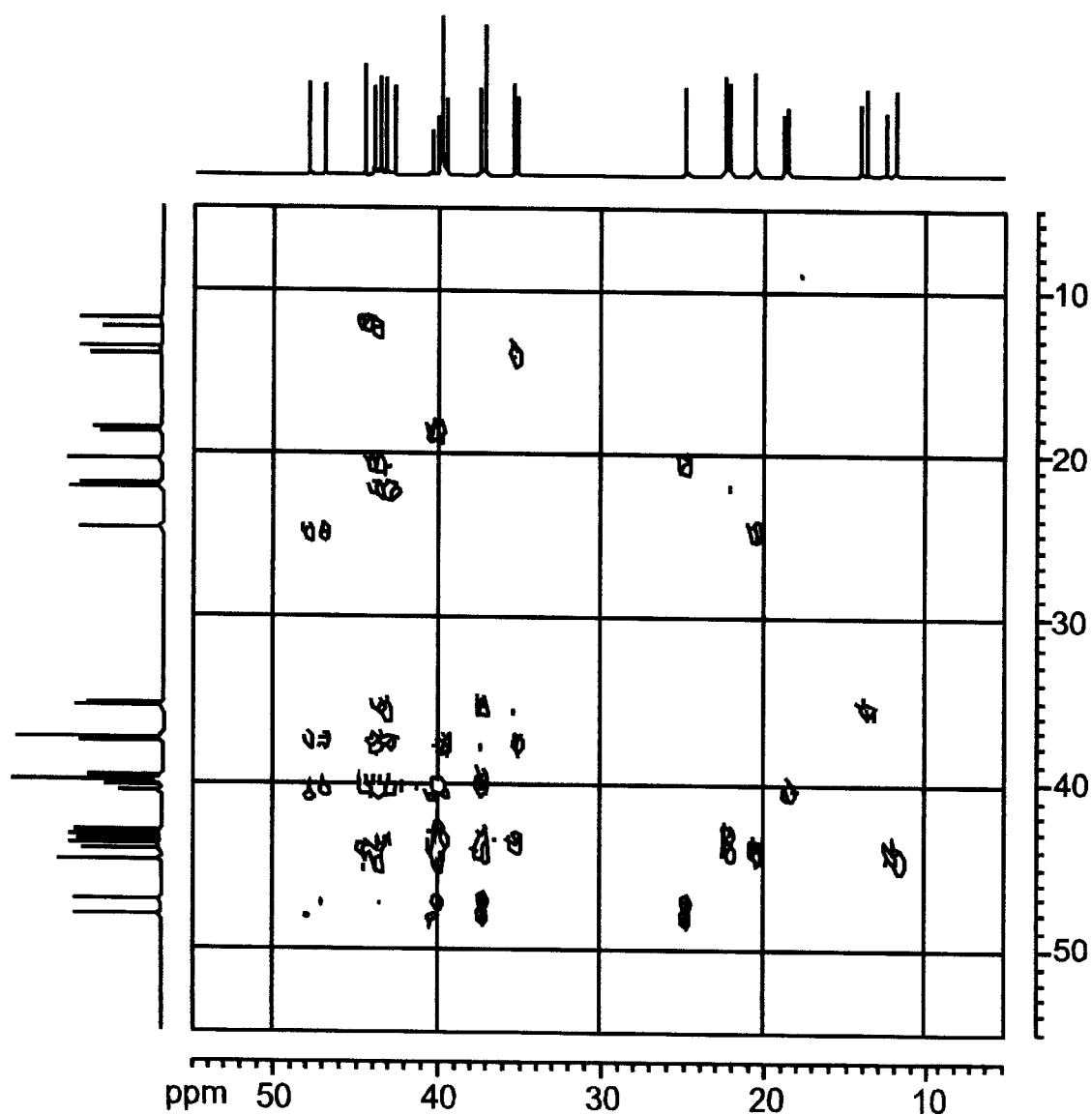
FIG. 14. $^{13}$C—$^{13}$C two-dimensional NMR spectrogram of component C.
Figure 15:
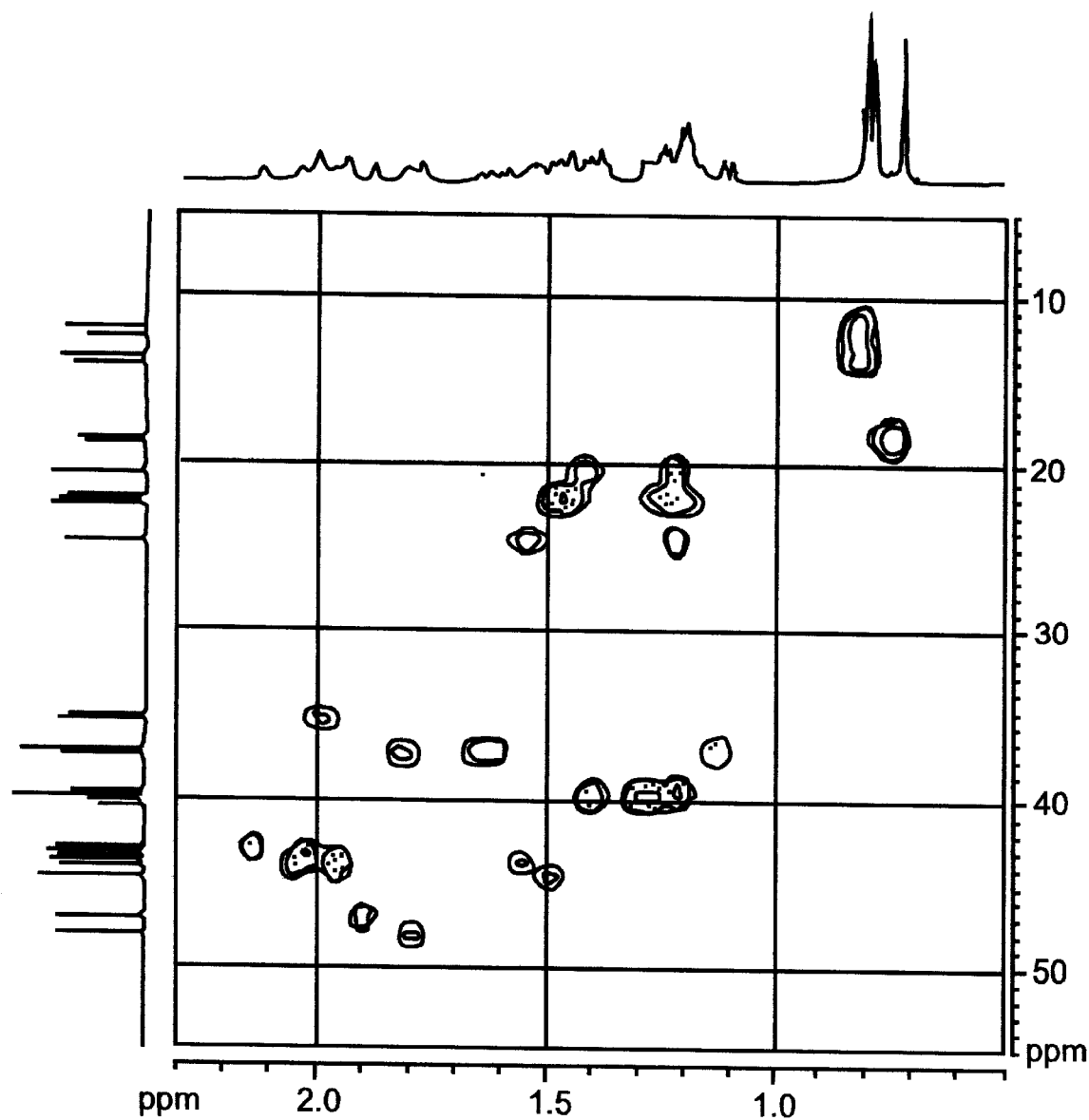
FIG. 15. $^1$H—$^{13}$C two-dimensional NMR spectrogram of component C.

FIGS. 11–15 show each spectrogram of mass chromatogram, $^1$H-NMR, $^{13}$C-NMR, $^{13}$C—$^{13}$C-NMR, and $^1$H—$^{13}$C-NMR used for the structural analysis.

The result of the analysis of the hydrogenated dimer prepared in the Example 3 with gas chromatography showed contents of 45 weight percent of the component B and 45 weight percent of the component C.

Example 4

Table 1 shows the measured result of general properties and a traction coefficient of the fraction, that contains 88 weight percent of the component B and 10 weight percent of the component C, yielded by the rectification for seperation of the Example 3.

Example 5

140 g of hydrogenated dimer was yielded by replacing the catalyst of 8 g of diethyl ether complex of boron trifluoride for dimerization of the Example 1 to 32 g of tin tetrachloride. The result of the analysis of the hydrogenated dimer with gas chromatography showed contents of 20 weight percent of the component A and 60 weight percent of the component B. Table 1 shows the result of measurement of general properties and a traction coefficient of the fraction.

Example 6

280 g of hydrogenated dimer was yielded by replacing the catalyst of 8 g of diethyl ether complex of boron trifluoride for dimerization to 20 g of 116% polyphosphoric acid by reaction under 50° C. The result of the analysis of the hydrogenated dimer with mass spectrum analysis and nuclear magnetic resonance spectrum analysis showed bicyclo[2.2.1]heptane derivative represented by said formula (I). Table 1 shows the measured result of general properties and a traction coefficient of the fraction.

Example 7

200 g of hydrogenated dimer was yielded by replacing the catalyst of 8 g of diethyl ether complex of boron trifluoride for dimerization to 8 g of a 1.5 water complex of boron trifluoride by reaction under 10° C. The result of the analysis of the hydrogenated diner with mass spectrum analysis and nuclear magnetic resonance spectrum analysis showed bicyclo[2.2.1]heptane derivative represented by said formula (I). Table 1 shows the measured result of general properties and a traction coefficient of the fraction.

Example 8

240 g of hydrogenated diner was yielded by replacing the hydrogenating reaction under the condition of 250° C. for 6 hours to the condition of 160° C. for 4 hours. The result of the analysis of the hydrogenated diner with mass spectrum analysis and nuclear magnetic resonance spectrum analysis showed bicyclo[2.2.1]heptane derivative represented by said formula (I). Table 1 shows the result of measurement of general properties and a traction coefficient of the fraction.

Example 9

Crotonaldehyde (350.5 g=5 mol) and dicyclopentadiene (198.3 g=1.5 mol) were put in 1 L, stainless steel-made autoclave to react by mixing for 3 hours under 170° C. The reaction solution was cooled to a room temperature, 2 g of a 5% ruthenium carbon catalyst [NE Chem Cat, K.K. made] was added, and finally, hydrogenation was carried out under a hydrogen pressure of 70 kg/cm$^2$G and reaction temperature of 180° C. for 4 hours. After cooling, the catalyst was filtered to separate, the filtrate was distilled under reduced pressure to yield 242 g of a fraction under 70° C./0.9 mmHg. The result of mass spectrum analysis and nuclear magnetic resonance spectrum analysis of the fraction showed that the fraction is 2-hydroxy methyl-3-methylbicyclo[2.2.1]heptane and 3-hydroxy methyl-2-methylbicyclo[2.2.1]heptane.

Next, 15 g of γ-alumina [Nikka Seikou, K.K. made, Norton Alumina SA-6273] was put in a quartz glass-made flow reaction tube under atmospheric pressure, with an outer diameter of 20 mm and a length of 500 mm to start dehydration reaction going under a reaction temperature of 270° C. and weight hourly space velocity (WHSV)=1.07 hr$^{-1}$, and finally, 196 g of the dehydrating reaction product of 2-hydroxymethyl-3-methylbicyclo[2.2.1]heptane and 3-hydroxymethyl-2-methylbicyclo[2.2.1]heptane were yielded containing 65 weight percent of 2-methylene-3-methylbicyclo[2.2.1]heptane and 3-methylene-2-methylbicyclo[2.2.1]heptane and 28 weight percent of 2,3-dimethylbicyclo[2.2.1]hept-2-ene.

Production of Hydrogenated Dimer

Activated clay (9.5 g) [Mizusawa Kagaku, K.K. made Galeon Earth NS] and the olefin compound (190 g) yielded from said steps were put in 500 ml four-neck flask and stirred under 145° C. for 3 hours to start dimerization reaction going. Activated clay was filtered from the reaction mixture, 6 g of nickel/diatomite catalyst [Nikki Kagaku, K.K. made, N-113] was added for hydrogenation in 1-L autoclave, and finally, hydrogenation reaction was started under the condition of 40 kg/cm$^2$G of hydrogen pressure, reaction temperature of 160° C. and reaction time of 4 hours. After the completion of reaction, the catalyst was removed by filtration to distill the filtrate under reduced pressure to yield 116 g of the hydrogenated dimer of 126–128° C. b.p./0.2 mmHg fraction. The result of the analysis of the hydrogenated dimer with mass spectrum analysis and nuclear magnetic resonance spectrum analysis showed bicyclo[2.2.1]heptane derivative represented by said formula (I). The table 1 shows the measured result of general properties and a traction coefficient of the dimer hydride.

Example 10

280 g of hydrogenated dimer was yielded by replacing the condition of dimerization reaction under 50° C. in the Example 6 to a condition under 100° C. The result of the analysis of the hydrogenated dimer with mass spectrum analysis and nuclear magnetic resonance spectrum analysis showed bicyclo[2.2.1]heptane derivative represented by said formula (I). Table 1 shows the result of measurement of general properties and a traction coefficient of the fraction.

The traction coefficient was measured by using a twin-cylinder friction tester in said Examples. The traction coefficient was known by measuring tangential force, that is, traction force, generated between these two cylinders with a constant speed for the one of contacting two cylinders with a same size (a driven, Japanese drum-shaped, cylinder with the radius of curvature of 10 mm and a driving cylinder with a flat type without crowning; diameter of 52 mm and thickness of 6 mm) and with a continuously changed rotation speed of the other, applying 98.0 N with a weight fitted to the contact point of both the cylinders. The cylinders were made by polishing to a mirror-smooth state of bearing steel SUJ-2 and showed average peripheral speed in girth of 6.8 m/s, and the maximum Herzian contact pressure of 1.23 GPa. The traction coefficient under fluid temperature (oil temp) 140° C., was measured by heating an oil tank to increase the oil temperature from 40° C. to 140° C. and the traction coefficient was known at slide/oil ratio of 5%.

of viscosity under low temperature to allow to use as a CVT oil for a traction drive in the world from cold and tropical regions. Various bicyclo[2.2.1]heptane derivatives can be efficiently prepared by the method according to the invention.

What is claimed is:

1. A compound selected from the group consisting of exo-2-methyl-exo-3-methyl-endo-2-[(endo-2-methylbicyclo[2.2.1]hept-exo-3-yl)methyl]bicyclo[2.2.1]heptane, exo-2-methyl-exo-3-methyl-endo-2-[(endo-3-methylbicyclo[2.2.1]hept-exo-2-yl)methyl]bicyclo[2.2.1]heptane, endo-2-methyl-exo-3-methyl-exo-2-[(exo-3-methylbicyclo-[2.2.1]hept-exo-2-yl)methyl]bicyclo[2.2.1]heptane, endo-2-methyl-exo-3-methyl-exo-2-[(exo-2-methylbicyclo[2.2.1]hept-exo-3-yl)methyl]bicyclo[2.2.1]heptane, endo-2-methyl-exo-3-methyl-exo-2-[(endo-3-methylbicyclo[2.2.1]hept-endo-2-yl)methyl]bicyclo[2.2.1]heptane, and endo-2-methyl-exo-3-methyl-exo-2-[(endo-2-methylbicyclo[2.2]hept-endo-3-yl)methyl]bicyclo[2.2.1]heptane.

2. Exo-2-methyl-exo-3-methyl-endo-2-[(endo-3-methylbicyclo[2.2.1]hept-exo-2-yl)methyl]bicyclo[2.2.1]heptane.

3. Exo-2-methyl-exo-3-methyl-endo-2-[(endo-2-methylbicyclo[2.2.1]hept-exo-3-yl)methyl]bicyclo[2.2.1]heptane.

TABLE 1

| | Example | | | | | |
|---|---|---|---|---|---|---|
| | 1 | 2 | 4 | 5 | 6 | 7 |
| Kinematic viscosity (@ 40° C.) mm²/s | 16.97 | 17.76 | 21.33 | 18.01 | 19.80 | 18.50 |
| Kinematic viscosity (@ 100° C.) mm²/s | 3.519 | 3.664 | 4.022 | 3.637 | 3.784 | 3.665 |
| Viscosity index | 74 | 83 | 73 | 73 | 62 | 67 |
| Pour point ° C. | −55.0 | −55.0 | −50.0 | −52.5 | −47.5 | −50.0 |
| Low temp. viscosity (@ −40° C.) mm²/s | 41,000 | 39,000 | 110,000 | 54,000 | 130,000 | 74,000 |
| Density (@ 20° C.) g/mm | 0.9580 | 0.9562 | 0.9643 | 0.9571 | 0.9603 | 0.9563 |
| Traction coefficient (@ 140° C.) | 0.078 | 0.079 | 0.082 | 0.079 | 0.081 | 0.080 |

| | Example | | |
|---|---|---|---|
| | 8 | 9 | 10 |
| Kinematic viscosity (@ 40° C.) mm²/s | 24.16 | 22.38 | 20.73 |
| Kinematic viscosity (@ 100° C.) mm²/s | 4.275 | 4.007 | 3.803 |
| Viscosity index | 67 | 52 | 47 |
| Pour point ° C. | −45.0 | −45.0 | −45.0 |
| Low temp. viscosity (@ −40° C.) mm²/s | 200,000 | 200,000 | 200,000 |
| Density (@ 20° C.) g/mm | 0.9676 | 0.9630 | 0.9605 |
| Traction coefficient (@ 140° C.) | 0.083 | 0.083 | 0.082 |

Bicyclo[2.2.1]heptane derivatives or fluid for traction drive according to the invention has a high traction coefficient under high temperature and an excellent characteristic 4. Endo-2-methyl-exo-3-methyl-exo-2-[(exo-3-methylbicyclo[2.2.1]hept-exo-2-yl)methyl]bicyclo[2.2.1]heptane.

5. Endo-2-methyl-exo-3-methyl-exo-2-[(exo-2-methylbicyclo[2.2.1]hept-exo-3-yl)methyl]bicyclo[2.2.1]heptane.

6. Endo-2-methyl-exo-3-methyl-exo-2-[(endo-3-methylbicyclo[2.2.1]hept-endo-2-yl)methyl]bicyclo[2.2.1]heptane.

7. Endo-2-methyl-exo-3-methyl-exo-2-[(endo-3-methylbicyclo[2.2.1]hept-endo-3-yl)methyl]bicyclo[2.2.1]heptane.

8. A mixture of exo-2-methyl-exo-3-methyl-endo-2-[(endo-3-methylbicyclo[2.2.1]hept-exo-2-yl)methyl]bicyclo[2.2.1]heptane and exo-2-methyl-exo-3-methyl-endo-2-[(endo-2-methylbicyclo[2.2.1]hept-exo-3-yl)methyl]bicyclo[2.2.1]heptane.

9. A mixture of endo-2-methyl-exo-3-methyl-exo-2-[(exo-3-methylbicyclo[2.2.1]hept-exo-2-yl)methyl]bicyclo[2.2.1]heptane and endo-2-methyl-exo-3-methyl-exo-2-[(exo-2-methylbicyclo[2.2.1]hept-exo-3-yl)methyl]bicyclo[2.2.1]heptane.

10. A mixture of endo-2-methyl-exo-3-methyl-exo-2-[(endo-3-methylbicyclo[2.2.1]hept-endo-2-yl)methyl]bicyclo[2.2.1]heptane and endo-2-methyl-exo-3-methyl-exo-2-[(endo-2-methylbicyclo[2.2.1]hept-endo-3-yl)methyl]bicyclo[2.2.1]heptane.

11. A method for preparing a bicyclo[2.2.1]heptane derivative represented by the following formula

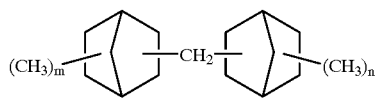

wherein m represents 2 or 3 and n represents 1 or 2, the method comprising dimerizing a methylene- and methyl-substituted bicyclo[2.2.1]heptane ring compound and/or a methyl-substituted bicyclo[2.2.1]heptene ring compound in the presence of an acid catalyst at a temperature of 60° C. or lower and hydrogenating the produced dimer in the presence of a hydrogenation catalyst at a temperature of 200–300° C.

12. A method for preparing a bicyclo[2.2.1]heptane derivative according to claim 11, wherein a methylene- and methyl-substituted bicyclo[2.2.1]heptane ring compound is 2-methylene-3-methylbicyclo[2.2.1]heptane and/or 3-methylene-2-methylbicyclo[2.2.1]heptane.

13. A method for preparing a bicyclo[2.2.1]heptane derivative according to claim 11, wherein the methyl-substituted bicyclo[2.2.1]heptene ring compound is 2,3-dimethylbicyclo[2.2.1]hept-2-ene.

14. A method for preparing the bicyclo[2.2.1]heptane derivative according to claim 11, wherein the acid catalyst is a Lewis acid.

15. A method for preparing a bicyclo[2.2.1]heptane derivative according to claim 11, wherein the catalyst for hydrogenation is a nickel catalyst.

16. A fluid for a traction drive consisting of a synthetic oil having the following physical properties:

(1) a molecular weight of at least 210;

(2) a kinematic viscosity at 40° C. of 10–25 $m^2$/s;

(3) a viscosity index of at least 60;

(4) a pour point of no more than −40° C.;

(5) a density at 20° C. of at least 0.93 g/cm$^3$; and (6) a traction coefficient at 140° C. that is at least 90% of the traction coefficient of 2,4-dicyclohexyl-2-methylpentane.

17. A fluid for a traction drive according to claim 16, wherein the synthetic oil is a hydrogenated dimer of at least one alicyclic compound selected from the group consisting of a bicyclo[2.2.1]heptane ring compound, a bicyclo[3.2.1]octane ring compound, a bicyclo[3.3.0]octane ring compound, and a bicyclo[2.2.2]octane ring compound.

18. A fluid for a traction drive according to claim 16, wherein the synthetic oil is a compound of the following formula

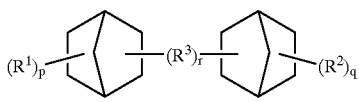

wherein both $R^1$ and $R^2$ represent hydrogen atoms or $C_1$–$C_3$ alkyl groups, $R^3$ represents a methylene group, an ethylene group, or a trimethylene group that may be substituted by a methyl group or an ethyl group in a side chain, r represents 0 or 1, and both p and q represent integral numbers of 1–3.

19. A fluid for a traction drive consisting of a derivative of bicyclo[2.2.1]heptane represented by the following formula

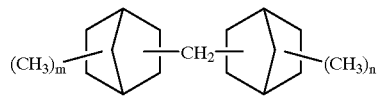

wherein m represents 2 or 3 and n represents 1 or 2.

* * * * *